US008891728B2

(12) United States Patent
Ogura

(10) Patent No.: US 8,891,728 B2
(45) Date of Patent: Nov. 18, 2014

(54) SPECIMEN SUPPORTING MEMBER FOR X-RAY MICROSCOPE IMAGE OBSERVATION, SPECIMEN CONTAINING CELL FOR X-RAY MICROSCOPE IMAGE OBSERVATION, AND X-RAY MICROSCOPE

(75) Inventor: Toshihiko Ogura, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 291 days.

(21) Appl. No.: 13/581,141

(22) PCT Filed: Feb. 23, 2011

(86) PCT No.: PCT/JP2011/053973
§ 371 (c)(1),
(2), (4) Date: Aug. 24, 2012

(87) PCT Pub. No.: WO2011/105421
PCT Pub. Date: Sep. 1, 2011

(65) Prior Publication Data
US 2012/0321037 A1 Dec. 20, 2012

(30) Foreign Application Priority Data

Feb. 24, 2010 (JP) .................................. 2010-038375

(51) Int. Cl.
*G21K 7/00* (2006.01)
*G01N 23/225* (2006.01)

(52) U.S. Cl.
CPC ........... *G21K 7/00* (2013.01); *H01J 2237/2445* (2013.01); *G01N 23/2251* (2013.01); *H01J 2237/28* (2013.01); *H01J 2237/20* (2013.01)
USPC ............................................ 378/43; 378/208

(58) Field of Classification Search
CPC ... G21K 7/00; G21K 2207/00; G01N 23/223; G01N 23/2251; G01N 23/2076; G01N 23/2204; H01J 37/256; H01J 37/20; H01J 37/28; H01J 2237/20; H01J 2237/2445; H01J 2237/2807
USPC .................................................... 378/43, 208
See application file for complete search history.

(56) References Cited

U.S. PATENT DOCUMENTS 2,843,751 A * 7/1958 Martin et al. .................... 378/43
5,044,001 A * 8/1991 Wang .............................. 378/43
(Continued)

FOREIGN PATENT DOCUMENTS

JP 2 138856 5/1990
JP 6 180400 6/1994
(Continued)

OTHER PUBLICATIONS

Ogura, T., "A high contrast method of unstained biological samples under a thin carbon film by scanning electron microscopy," Biochemical and Biophysical Research Communications, vol. 377, pp. 79-84, (Oct. 1, 2008).
(Continued)

*Primary Examiner* — Jack Berman
(74) *Attorney, Agent, or Firm* — Oblon, Spivak, McClelland, Maier & Neustadt, L.L.P.

(57) ABSTRACT

A specimen supporting member (10) includes: a specimen supporting film (11) such as a silicon nitride film, a carbon film, and a polyimide film; an X-ray radiation film (13) provided on one principal surface of the specimen supporting film, and for radiating a characteristic X-ray in a soft X-ray region upon irradiation with charged particles; and a specimen adsorption film (12) which is a metal film provided on another principal surface of the specimen supporting film (11), and which fixes by adsorption a specimen (1) to be observed. Since a protein which is a constitutive substance of a biological specimen has a characteristic to easily adsorb to a metallic ion, a specimen adsorption film (12) is formed on one principal surface of the specimen supporting film (11) so that an observation specimen adsorbs thereto.

32 Claims, 20 Drawing Sheets

(56) References Cited

U.S. PATENT DOCUMENTS

| | | | |
|---|---|---|---|
| 5,528,646 A * | 6/1996 | Iketaki et al. | 378/43 |
| 5,832,052 A * | 11/1998 | Hirose et al. | 378/43 |
| 6,163,590 A | 12/2000 | Wilkins | |
| 2001/0001010 A1 | 5/2001 | Wilkins | |
| 2010/0116140 A1 | 5/2010 | Arai et al. | |

FOREIGN PATENT DOCUMENTS

| | | |
|---|---|---|
| JP | 8 43600 | 2/1996 |
| JP | 2001 519022 | 10/2001 |
| JP | 2003 344314 | 12/2003 |
| JP | 2009 18290 | 1/2009 |
| WO | WO 98/45853 A1 | 10/1998 |
| WO | 2007 141868 | 12/2007 |
| WO | 2010 087359 | 8/2010 |
| WO | 2010 134282 | 11/2010 |

OTHER PUBLICATIONS

Shimizu, H., et al., "Observation of Living Cells with X-ray Microscopy," Medical Imaginig Technology, vol. 17, No. 3, pp. 211-216, (May 1999) (with partial English translation).
Jacobsen, C., "Soft x-ray microscopy," Trends in Cell Biology, vol. 9, pp. 44-47, (Feb. 1999).
Chao, W., et al., "Soft X-ray microscopy at a spatial resolution better than 15nm," Nature, vol. 435, No. 30, pp. 1210-1213, (2005).
International Search Report Issued May 31, 2011 in PCT/JP11/53973 Filed Feb. 23, 2011.
Extended European Search Report issued Dec. 6, 2013, in European Patent Application No. 11747381.9.
Toshihiko Ogura., "Measurement of the unstained biological sample by a novel scanning electron generation X-ray microscope based on SEM", Biochemical and Biophysical Research Communications, XP-026211121, vol. 385, No. 4, Aug. 7, 2009, pp. 624-629.

* cited by examiner

SPECIMEN SUPPORTING MEMBER FOR X-RAY MICROSCOPE IMAGE OBSERVATION, SPECIMEN CONTAINING CELL FOR X-RAY MICROSCOPE IMAGE OBSERVATION, AND X-RAY MICROSCOPE

TECHNICAL FIELD

The present invention relates to an observation technique of X-ray microscope image, and particularly to a technique suitable for the observation of a high-resolution X-ray microscope image of a biological specimen in an aqueous solution.

BACKGROUND ART

An X-ray microscope can observe a specimen in an aqueous solution at a higher resolution compared with an optical microscope. Particularly, soft X-ray having a wavelength in a range of 2.3 to 4.4 nm (corresponding to 284 to 540 eV), which is generally called as the "water window", has a characteristic that its absorption coefficient significantly differs among materials constituting a living body, and that while it passes through water, it hardly passes through protein etc. due to large absorption by carbon and nitrogen.

Using such soft X-ray in the "water window" region will allow an object containing water (a living body specimen and a specimen in a solution) to be observed as it is, and in addition to that, will allow observation at a higher resolution than that of an optical microscope since its wavelength is shorter than visible light. From that reason, development of a soft X-ray microscope utilizing X-ray in the wavelength region of "water window" has been promoted (for example, Non Patent Literature 1: MAJIMA et. al, "Observation of living cells with X-ray Microscopy," Medical Imaging Technology, Vol. 17, No. 3, p. 211-216, (1999)).

Besides the soft X-ray in the wavelength range of "water window", a soft X-ray in the "carbon window" wavelength region (5.0 to 4.5 nm), which exhibits lower absorption by carbon, and a soft X-ray in a further shorter wavelength region (0.6 to 2.3 nm) are effective in the observation of biological specimens.

X-ray microscopy is primarily classified into a method of narrowing down an X-ray beam by using a condensing system such as a zone plate etc. and applying it to a specimen (a light condensing system), and a method of applying an X-ray beam from a point source to a specimen (a point light source system).

X-ray microscopes of light condensing system are classified into a radiation transmission type and a scanning transmission type (Non Patent Literature 2: Chris Jacobsen, "Soft x-ray microscopy," Trend in Cell Biology, Vol. 9, p. 44-47 (1999)), and the resolution in this method depends on the processing accuracy of the zone plate, and a theoretical limit thereof is predicted to be 10 to 15 nm (Non Patent Literature 3: W. Chao et al., "Soft X-ray microscopy at a spatial resolution better than 15 nm," Nature, Vol. 453, p. 1210-1213 (2005)).

On the other hand, while the method of utilizing a point light source is classified into a method of generating X-ray with a laser and a method of generating X-ray with an electron beam, a method of observing a specimen with X-ray, which is generated by making an electron beam incident on a target, as a probe is being developed.

This method adopts a technique in which an electron beam is made directly incident on a specimen supporting film to generate X-ray, and the X-ray is made to irradiate a specimen adhered to the specimen supporting film opposite the electron beam incident direction (Patent Literature 1: Japanese Patent Laid-Open No. 8-43600, Patent Literature 2: Japanese Patent Application No. 2009-18290 specification, and Patent Literature 3: Japanese Patent Laid-Open No. 2-138856).

According to such a technique, since a charged particle beam which is narrowed to be extremely thin is made incident on a specimen supporting film thereby allowing the diffusion range of the charged particles to be suppressed, it is possible to achieve a high resolution. Moreover, since mounting a plurality of X-ray detectors at various angles and locations below the specimen supporting film will enable the acquisition of inclined images depending on the mounting angle thereof, inclined images of the same number as that of the detectors are obtained by one charged beam scanning, making it possible to recreate a three-dimensional structure of the specimen to be observed (Patent Literature 2: Japanese Patent Application No. 2009-18290 Specification).

As the specimen supporting member (supporting film) to be used for such soft X-ray microscope observation, a silicon nitride film has been widely used. Since the silicon nitride film is excellent in pressure resistance, even when it is provided at a window portion of the specimen containing cell of which interior is under atmospheric pressure, it will cause no hindrance for use in a microscope apparatus which is to be put under vacuum. For example, in the invention disclosed in Japanese Patent Laid-Open No. 6-180400 (Patent Literature No. 4), a specimen cell in which two sheets of silicon nitride film are fixed in parallel with a predetermined interval therebetween, and an observation specimen is contained in the spacing with aqueous solution to be sealed is introduced into a soft X-ray microscope apparatus of which interior is under vacuum.

Meanwhile, when a specimen in an aqueous solution is observed at a high resolution, it is necessary to fix the specimen to the supporting member to suppress the deflections of an observed image caused by Brownian motion, and it is an essential factor that such a supporting film for fixing the specimen to the specimen supporting member is as thin as possible and highly durable, and further has a high transparency to X-ray.

Conventionally, organic matters such as concanavalin A and polyimidines have been used as the fixing agent for a biological specimen. However, since such organic matters contain a large amount of carbon and nitrogen, soft X-ray in the above described water window region is apt to be absorbed, thereby significantly reducing the contrast of a resulting observation image. Moreover, since the molecular size is as large as several tens of nm, a problem also exists in that the structure of such specimen fixing agent itself is observed at the time of high resolution observation. Further, they also have drawbacks that they are susceptible to external environments such as heat and ultra violet ray or humidity, and are lack of durability.

CITATION LIST

Patent Literature

Patent Literature 1: Japanese Patent Laid-Open No. 8-43600
Patent Literature 2: Japanese Patent Application No. 2009-18290 Specification
Patent Literature 3: Japanese Patent Laid-Open No. 2-138856
Patent Literature 4: Japanese Patent Laid-Open No. 6-180400

Non Patent Literature

Non Patent Literature 1: MAJIMA et. al, "Observation of living cells with X-ray Microscopy," Medical Imaging Technology, Vol. 17, No. 3, p. 211-216, (1999)

Non Patent Literature 2: Chris Jacobsen, "Soft x-ray microscopy," Trend in Cell Biology, Vol. 9, p. 44-47 (1999)

Non Patent Literature 3: W. Chao et al., "Soft X-ray microscopy at a spatial resolution better than 15 nm," Nature, Vol. 453, p. 1210-1213 (2005)

SUMMARY OF INVENTION

Technical Problem

The present invention has been made in view of the above described problems, and has its object to provide a specimen supporting member for X-ray microscope image observation, which is excellent in the transparency and durability to soft X-ray in the "water window" region and, furthermore, is able to mitigate damages to the observation specimen caused by the application of charged particles, and which is suitable for X-ray microscope image observation of a biological specimen.

Moreover, it is a further object of the present invention to provide a specimen containing cell for X-ray microscope image observation and an X-ray microscope, using the above described specimen supporting member.

Solution to Problem

In order to solve the above described problems, the present invention utilizes a metal film which can easily adsorb protein which is a constitutive substance of a biological specimen as a specimen adsorption film of the specimen supporting member for X-ray microscope image observation.

That is, a specimen supporting member for X-ray microscope image observation of the present invention includes: a specimen supporting film; an X-ray radiation film provided on one principal surface of the specimen supporting film, and for radiating a characteristic X-ray in a soft X-ray region upon irradiation with charged particles; and a specimen adsorption film which is a metal film provided on another principal surface of the specimen supporting film, and which fixes by adsorption a specimen to be observed.

The above described specimen adsorption film may be a metal film predominantly composed of any element of nickel, cobalt, copper, zinc, iron, manganese, chromium, gold, or platinum.

The thickness of the above described specimen supporting member is not more than 300 nm.

The above described X-ray radiation film may be a film predominantly composed any of carbon, aluminum, scandium, titanium, vanadium, chromium, nickel, silicon, germanium, and oxides or nitrides thereof.

The above described X-ray radiation film may be embodied such that a plurality of films having different compositions are laminated.

Preferably, any of the above described plurality of films having different compositions has a thickness of not more than 100 nm.

Further, preferably, the above described plurality of films having different compositions are laminated from a charged-particle irradiation side in an order from a film of which principal element has a smaller atomic number to a film of which principal element has a larger atomic number. Furthermore, the above described plurality of films having different compositions may be embodied so as to be laminated from a charged-particle irradiation side in an order from a film made of a material having a lighter composition mass to a film made of a material having a heavier composition mass.

The specimen supporting member for X-ray microscope image observation of the present invention may be embodied to include a charged-particle shielding film between the specimen supporting film and the X-ray radiation film, or between the specimen supporting film and the specimen adsorption film.

The above described charged-particle shielding film is a film predominantly composed of any metal element of gold, platinum, palladium, osmium, tungsten, tin, cobalt, and nickel.

The above described specimen supporting film is a silicon nitride film, a carbon film, or a polyimide film.

The above described specimen supporting film has a thickness of, for example, not more than 200 nm.

A specimen containing cell for X-ray microscope image observation of the present invention includes: a cell upper portion provided with the above described specimen supporting member for X-ray microscope image observation; and a cell lower portion having an observation window opposed to the surface of the cell upper portion on the side of the specimen adsorption film, wherein the cell upper portion and the cell lower portion are disposed so as to have a gap of a predetermined width therebetween via a space member.

A specimen containing cell for X-ray microscope image observation of the present invention may be embodied such that an injection hole for introducing an observation specimen into a gap formed between the cell upper portion and the cell lower portion, and an air hole are provided.

Further, a specimen containing cell for X-ray microscope image observation of the present invention may be embodied to include a plurality of the injection holes, wherein a plurality of flow paths associated with each of the plurality of injection holes are provided.

Further, a specimen containing cell for X-ray microscope image observation of the present invention may be embodied to include: a conductive film provided in the vicinity of the injection hole; and a voltage application section for producing a potential difference between the conductive film and the specimen adsorption film to guide an observation specimen by electrophoresis from the injection hole to the specimen adsorption film side.

Further, a specimen containing cell for X-ray microscope image observation of the present invention may be embodied to include a pressure application section for pushing out an observation specimen from the injection hole to the specimen adsorption film side in the vicinity of the injection hole.

Preferably, a specimen containing cell for X-ray microscope image observation of the present invention includes a cell information recording section for recording information relating to a constitutive member of the specimen containing cell.

The above described cell-information recording section is printed or engraved at a location where reading from the outside is possible.

Further, the above described cell information recording section is a recording medium which is readable and writable from the outside.

An X-ray microscope of the present invention includes: a holder for holding the above described specimen supporting member or the specimen containing cell; a charged particle gun for making a charged particle beam converged and incident on the X-ray radiation film; a scanning mechanism section of the charged particle beam; an X-ray detector for detecting X-ray generated from the specimen supporting member as the result of incidence of the charged particle beam; and a signal processing section for forming an X-ray image based on the detected signal of X-ray.

Further, an X-ray microscope of the present invention includes: a holder for holding the above described specimen supporting member or the specimen containing cell; a charged particle gun for making a charged particle beam converged and incident on the X-ray radiation film; a scanning mechanism section of the charged particle beam; a photoelectric conversion section for photoelectrically converting X-ray, which is generated from the specimen supporting member as the result of incidence of the charged particle beam, into electrons; an electron beam detector for detecting the photoelectrically converted electron beam; and a signal processing section for forming an X-ray image based on the detected signal of the electron beam.

The X-ray microscope of the present invention may be embodied to include a plurality of the X-ray detectors, wherein the plurality of the X-ray detectors are disposed at locations where the observation specimen supported by the specimen supporting member is viewed from a different direction.

In this case, configuration may be such that the signal processing section includes an image processing section for forming a three-dimensional X-ray image based on detected X-ray signals from the plurality of the X-ray detectors.

Advantageous Effects of Invention

Since the present invention is configured to use a metal film which can easily adsorb protein which is a constitutive substance of a biological specimen as the observation-specimen adsorption film for the specimen supporting member for X-ray microscope image observation, it becomes possible to provide a specimen supporting member for X-ray microscope image observation suitable for X-ray microscope image observation of a biological specimen, which can shield charged particles passing through to the observation specimen side thereby reducing damages to the specimen, and at the same time, which is less likely to degrade the image quality of the X-ray observation image, and furthermore exhibits little deterioration due to temperature and humidity changes or ultra violet irradiation, etc., and also exhibits excellent durability.

Further, since the present invention is configured such that a cell information recording section for recording information relating to constitutive members is provided in advance in the specimen supporting member itself, or in the specimen containing cell for containing the specimen supporting member so that information of observation conditions and characteristic X-ray to be radiated are recorded such as by printing, it becomes possible to conveniently perform a high-resolution X-ray observation.

Thus, according to the present invention, it becomes possible that anybody conveniently acquires a high resolution X-ray image of a biological specimen in a solution.

DESCRIPTION OF EMBODIMENTS

Figure 1:
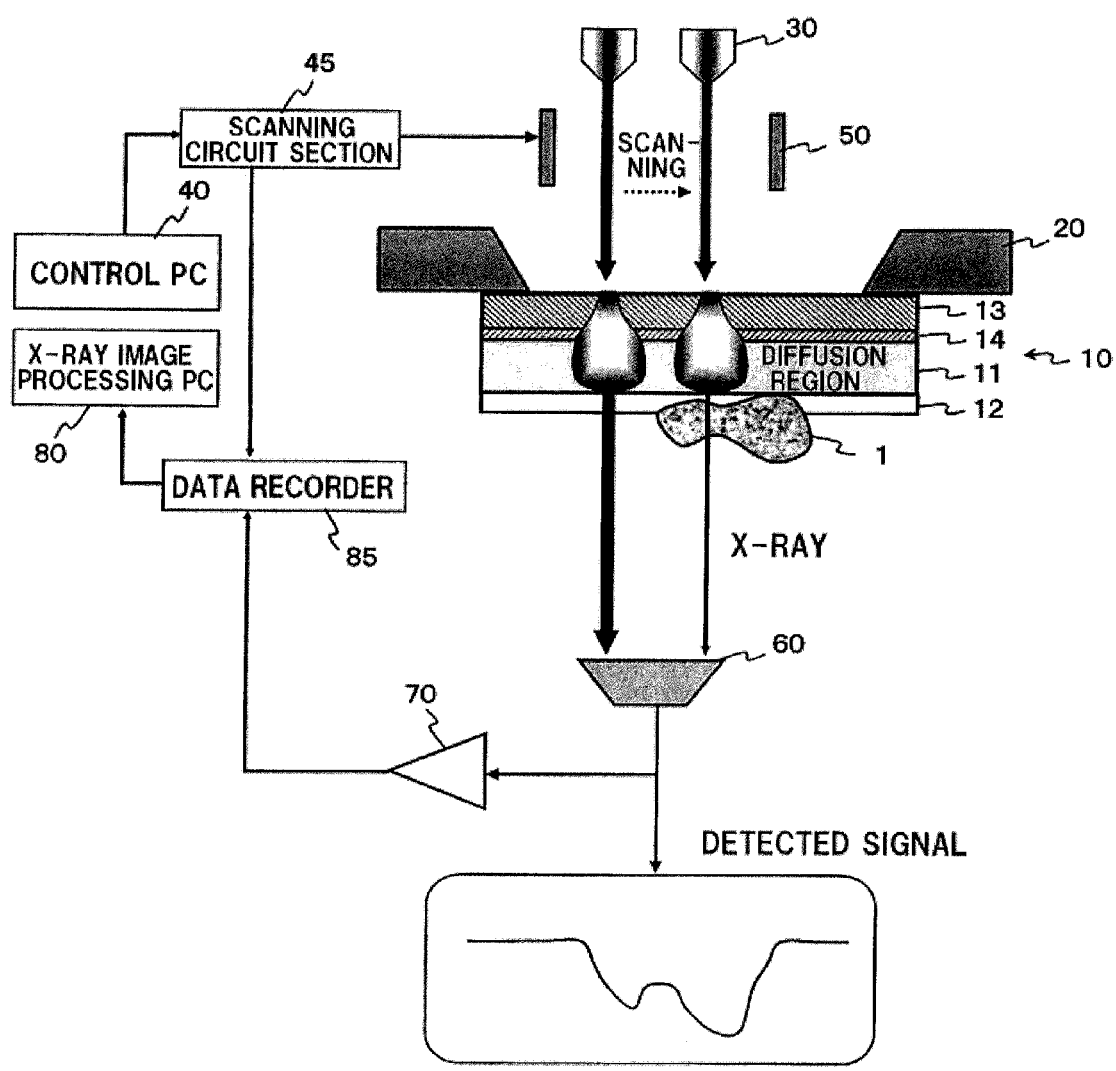
FIG. 1 is a block diagram to explain the outline of a configuration example of an X-ray microscope when performing X-ray microscope observation using a specimen supporting member relating to the present invention.

Hereafter, referring to the drawings, a specimen supporting member, a specimen containing cell, and an X-ray microscope for X-ray microscope image observation of the present invention will be described. While hereafter description will be made on the case where the charged particle beam is an electron beam, the charged particle beam is not limited to an electron beam and may be an ion beam provided that it generates a characteristic X-ray by the incidence on an X-ray radiation film described later.

FIG. 1 is a block diagram to explain the outline of a configuration example of an X-ray microscope when X-ray microscope observation is performed using a specimen supporting member relating to the present invention, which illustrates a configuration example in which an X-ray detector is provided in a scanning electron microscope (SEM). Accordingly, this scanning X-ray microscope can combine an SEM function.

The scanning X-ray microscope of the configuration example shown in FIG. 1 includes: a holder (20) for holding a specimen supporting member (10) that supports a specimen (1) to be observed; an electron gun (30) for causing an electron beam which is a beam of charged particles to be converged and incident on the specimen supporting member (10); a control PC (40) including a circuit section that produces a signal (scanning signal) for scanning the electron beam emitted from the electron gun (30); a deflection coil (50) for scanning the electron beam based on the scanning signal from the control PC (40); an X-ray detector (60) for detecting an X-ray generated in the specimen supporting member (10) upon irradiation with an incident electron beam; an amplifier (70) for amplifying a signal detected by the X-ray detector (60); and an X-ray image processing PC (80) for forming an X-ray image based on a detected X-ray signal.

The above described X-ray detector (60) may be configured to use, for example, an X-ray detector which can analyze energy spectra, such as a silicon drift detector and a PIN photodiode detector. Moreover, as normally being equipped in an ordinary SEM, a scanning mechanism section (not shown) which allows the positional adjustment etc. of the above described holder (20) in a plane and height directions.

As shown in FIG. 1, the specimen supporting member (10) for X-ray microscope image observation includes: for example, a specimen supporting film (11), such as a silicon nitride film, a carbon film, and a polyimide film, having a thickness of not more than 200 nm; an X-ray radiation film (13) provided on one principal surface of the specimen supporting film and for radiating a characteristic X-ray in a soft X-ray region by being irradiated with charged particles; and a specimen adsorption film (12) which is a metal film provided on another principal surface of the specimen supporting film (11) and for fixing by adsorption a specimen (1) to be observed.

As a metal film used as the specimen adsorption film (12), a metal film predominantly composed of any element of nickel, cobalt, copper, zinc, iron, manganese, chromium, gold, and platinum is suitable.

Generally, protein which is a constitutive substance of a biological specimen has a characteristic to easily adsorb to a metallic ion such as a nickel ion and a cobalt ion. Exploiting such characteristics, the present invention is configured such that the above described specimen adsorption film (12) is formed on one principal surface of the specimen supporting film (11) so as to cause an observation specimen to adsorb thereto. Using such specimen supporting member (10) will make it possible to fix an observation specimen only by dripping a solution containing a biological specimen onto the specimen adsorption film (12), or injecting it into a cell containing the specimen supporting member (10).

While metal such as nickel, cobalt, copper, zinc, iron, manganese, chromium, gold, platinum, etc. has a high absorption efficiency of charged particles, it has a high transmittance of soft X-ray in the "water window" region. For this reason, the specimen adsorption film (12) made up of any of those metals has the advantage that while it shields the charged particles being transmitted to the observation specimen side thereby reducing damages to the specimen, it is less likely to deteriorate the image quality of X-ray observation image.

Further, the above described metal film is less susceptible to degradation due to temperature and humidity changes, or ultraviolet irradiation, etc., and moreover is excellent in durability.

Moreover, although there is no specific limitation on the thickness of the specimen adsorption film (12), the thickness is preferably not more than 300 nm because if the thickness is excessively large, the absorption of soft X-ray in the "water window" region will become not negligible.

The X-ray radiation film (13) is irradiated with charged particles to radiate a characteristic X-ray having a wavelength of 0.6 to 6 nm. As such a film, a film predominantly composed any of carbon, aluminum, scandium, titanium, vanadium, chromium, nickel, silicon, germanium, and oxides or nitrides thereof is suitable. Particularly, since oxides and nitrides contain a large amount of atoms of oxygen and nitrogen, they are suitable as a radiation source of soft X-ray in the "water window" region.

Although, in the example shown in FIG. 1, the X-ray radiation film (13) is a film of single layer, it may be a multi-layered structure in which a plurality of layers having different compositions are laminated so as to generate various characteristic X-rays. In this case, since characteristic X-rays from all the films are needed to irradiate the observation specimen without remarkable attenuation, it is preferable that the thickness of each film is not more than 100 nm, and moreover, each film is laminated from a charged-particle irradiation side in an order from a film of which principal element has a smaller atomic number to a film of which principal element has a larger atomic number. Alternatively, in the case where the X-ray radiation film (13) is an oxide or nitride of metal or carbon, or an alloy, each film may be laminated from the charged particle irradiation side in an order from a film of which compositional material has a lighter mass to a film of which compositional material has a heavier mass.

Further, a charged-particle shielding film (14) predominantly composed of a metal element and having a thickness of about 5 to 100 nm may be provided between the specimen supporting film (11) and the X-ray radiation film (13), or between the specimen supporting film (11) and the specimen adsorption film (12) as shown in FIG. 1 for the purpose of further reducing the damages to the observation specimen (1) caused by charged particles. As such charged-particle shielding film (14), a film predominantly composed of any metal element of gold, platinum, palladium, osmium, tungsten, tin, cobalt, and nickel is preferable.

An electron beam is applied from the top face (front surface) of the X-ray radiation film (13) of the specimen supporting member (10), and the incident electrons spread while diffusing within the specimen supporting film (11) to reach the vicinity of the bottom surface of the specimen supporting film (11). The electron beam accelerating voltage when picking up an X-ray observation image is adjusted at a level at which the electrons incident on the specimen supporting film (11) will hardly pass through the specimen supporting film (11) and will reach the bottom surface of the specimen supporting film (11), thereby leading to a condition that the observation specimen (1) is not irradiated with the electron beam.

When such an acceleration voltage is applied, only the X-ray which is generated in the specimen supporting film (11) is emitted from the bottom surface of the specimen supporting film (11), and the incident electron beam (primary electron) is hardly emitted to outside the specimen supporting film (11). Thus, it is possible to avoid the primary electron from giving damage to the observation specimen (1) attached to the bottom surface of the specimen supporting film (11).

The X-ray emitted from the bottom surface of the specimen supporting film (11) will be at least partly absorbed by an area to which the observation specimen (1) adheres and, at the same time, will pass through the other areas without being changed.

As shown in FIG. 1, a detected signal of X-ray which is detected by an X-ray detector (60) disposed below the specimen supporting film (11) is amplified at an amplifier (70) to be fed to and recorded in a data recorder (85) that receives a scanning signal from a scanning circuit section (45), and an X-ray image is formed by an X-ray image processing PC (80) based on the detected signal (and the scanning signal). That is, by measuring X-ray signal intensities association with the irradiation position of each electron beam based on the scanning signal of electron beam, it becomes possible to obtain an X-ray image of the observation specimen (1). Moreover, since the electron beam emitted from an electron gun (30) can scan a desired range on the specimen supporting film (11) by a deflection coil (50), the intensity of X-ray detected by the X-ray detector (60) is relatively weak in a region to which the observation specimen (1) adheres, and is relatively stronger in other regions so that the X-ray image formed by the X-ray image processing PC (80) will include information about the shape and structure etc. of the observation specimen (1).

In the configuration example shown in FIG. 1, although only one X-ray detector is provided, configuration may be such that a plurality of X-ray detectors are provided, and those plurality of X-ray detectors are disposed at locations from which the observation specimen (1) supported by the specimen supporting film (11) is viewed from different directions.

Figure 2:
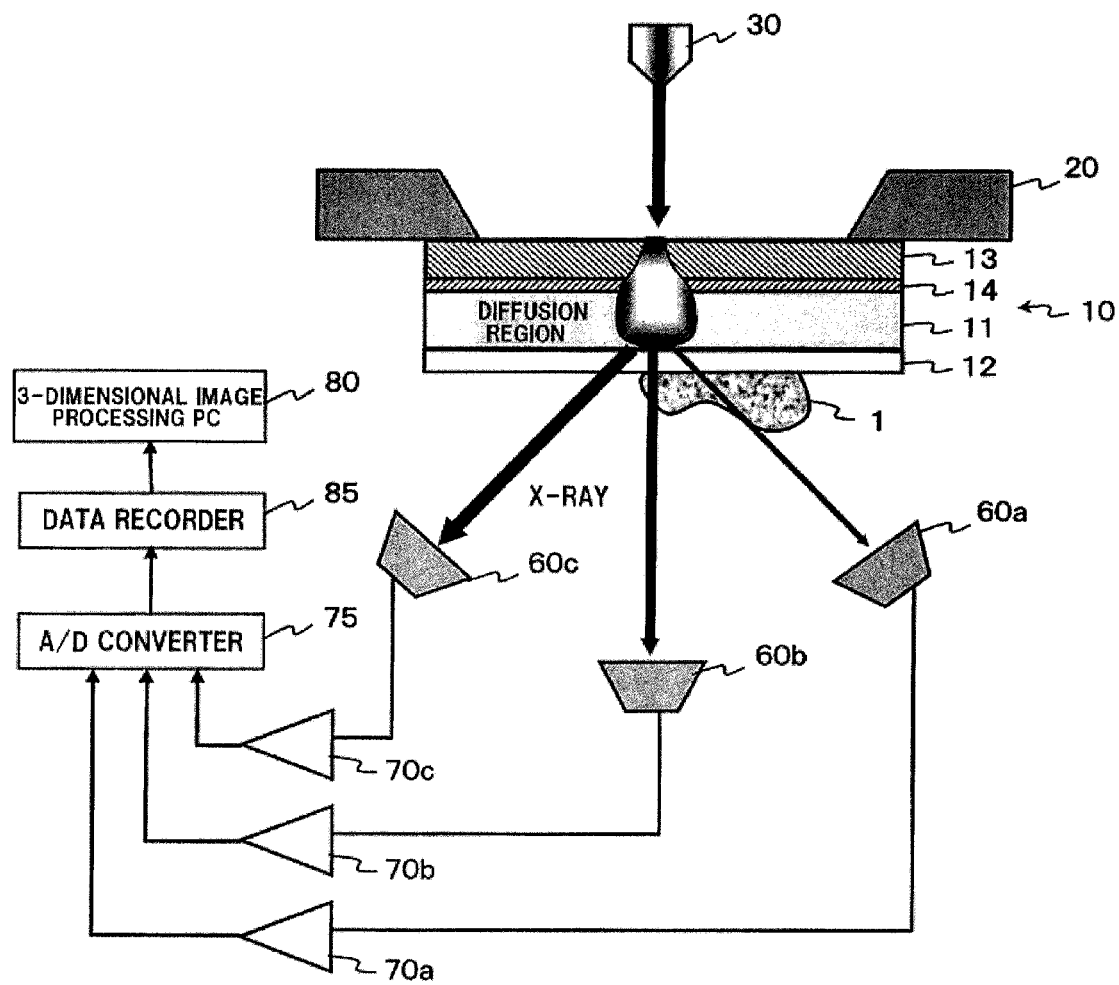
FIG. 2 is a diagram to explain a configuration example of an X-ray microscope which includes a plurality of X-ray detectors and enables the reconstruction of X-ray microscope image in three-dimension.

FIG. 2 is a diagram to explain a configuration example of an X-ray microscope which includes a plurality of X-ray detectors, and in the example shown in the figure, three X-ray detectors are provided (60a to 60c). In correspondence to this, three amplifiers (70a to 70c) are also provided, and configuration is made such that detected signals from these amplifiers are fed to an X-ray image processing PC (80: a three-dimensional image processing PC here) via an A/D converter (75) and a data recorder (85).

Although the X-rays from inside the specimen supporting film (11) are emitted in various directions, providing a plurality of X-ray detectors and disposing them at locations where the observation specimen (1) supported by the specimen supporting film (11) is viewed from different directions makes it possible to obtain a plurality of X-ray images (inclined images) depending on the angle to view the specimen. That is, inclined images of the same number as that of the detectors are obtained per one electron scanning, and it becomes possible to determine a three-dimensional structure of a specimen to be observed, and further, damages to the specimen will be still quite insignificant as described above.

Moreover, although an example of three X-ray detectors is shown in FIG. 2, it is also possible, as a matter of course, to dispose, for example, several tens or more of X-ray detectors thereby acquiring a large number of inclined images so that a highly accurate three-dimensional structure is determined.

Figure 3:
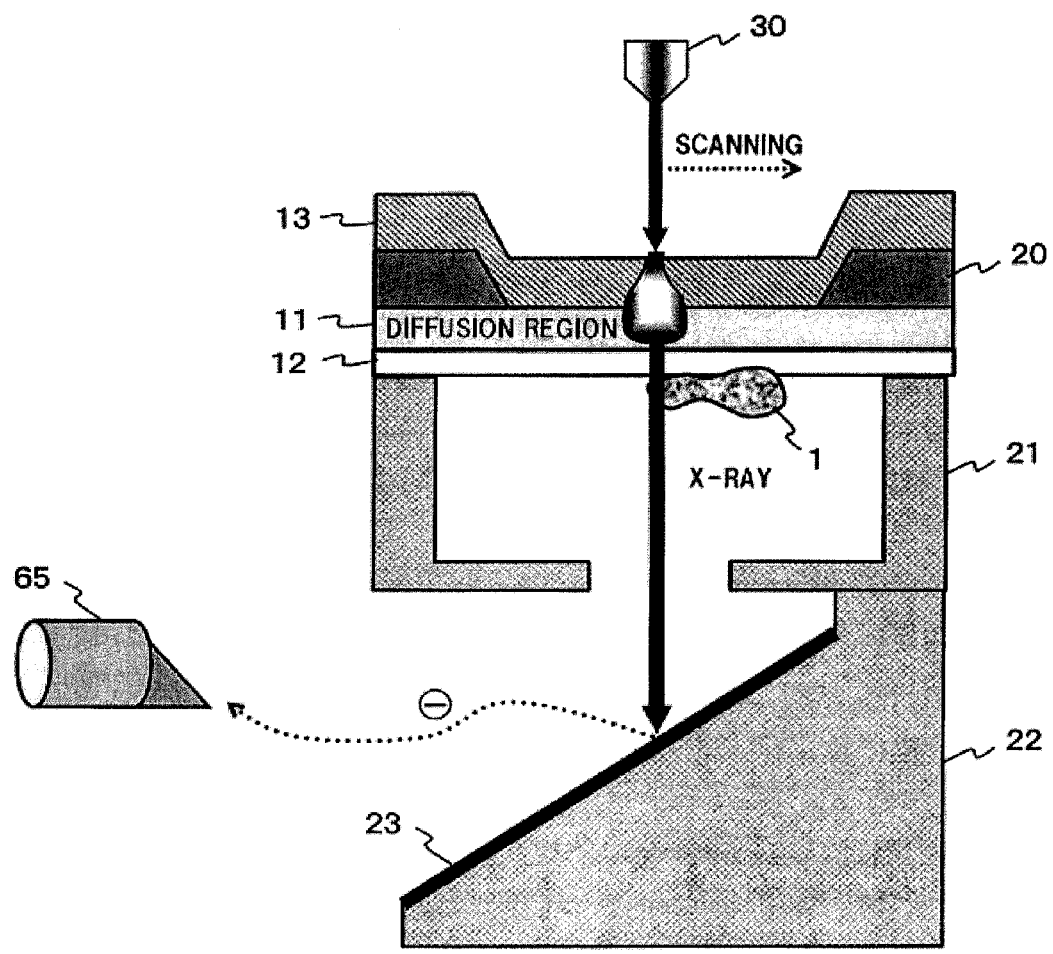
FIG. 3 is a diagram showing a configuration example for photoelectrically converting X-ray which has passed through the specimen to be observed, and observing an X-ray image by a secondary electron detector.

FIG. 3 is a diagram showing a part of the configuration of a mode of X-ray microscope which forms an X-ray image by detecting a secondary electron, and in this embodiment, a photoelectric conversion mechanism section (22) is provided below a holder supporting portion (21) for pacing the specimen supporting member (10), and a photoelectric conversion surface (23) for photoelectrically converting the X-ray, which has passed through the observation specimen (1), into electrons is provided in the photoelectric conversion mechanism section (22). The electrons generated at the photoelectric conversion surface (23) are detected by a secondary electron detector (65) and are fed to and recorded in a data recorder which receives scanning signals from a scanning circuit section as shown in FIG. 1, and an X-ray image is formed by an X-ray image processing PC based on the detected signal of electron beam (and scanning signal). It is noted that the lower portion of the holder supporting portion (21) shown in FIG. 3 functions as a so-called "aperture".

The X-ray microscope of this embodiment has the advantage that there is no need of adding particular improvements to a normal SEM. That is, although there is need of newly placing an X-ray detector and an amplifier inside an SEM in the case of the X-ray microscope shown in FIG. 1 or 2, adopting the embodiment of FIG. 3 obviates such efforts. Further, since a gold thin film can be used as the photoelectric conversion surface (23) and its structure can be made simple and compact, it is also possible to perform X-ray microscope observation by placing the photoelectric conversion mechanism section (22) as it is on a specimen stage which is used in a normal SEM.

Figure 4:
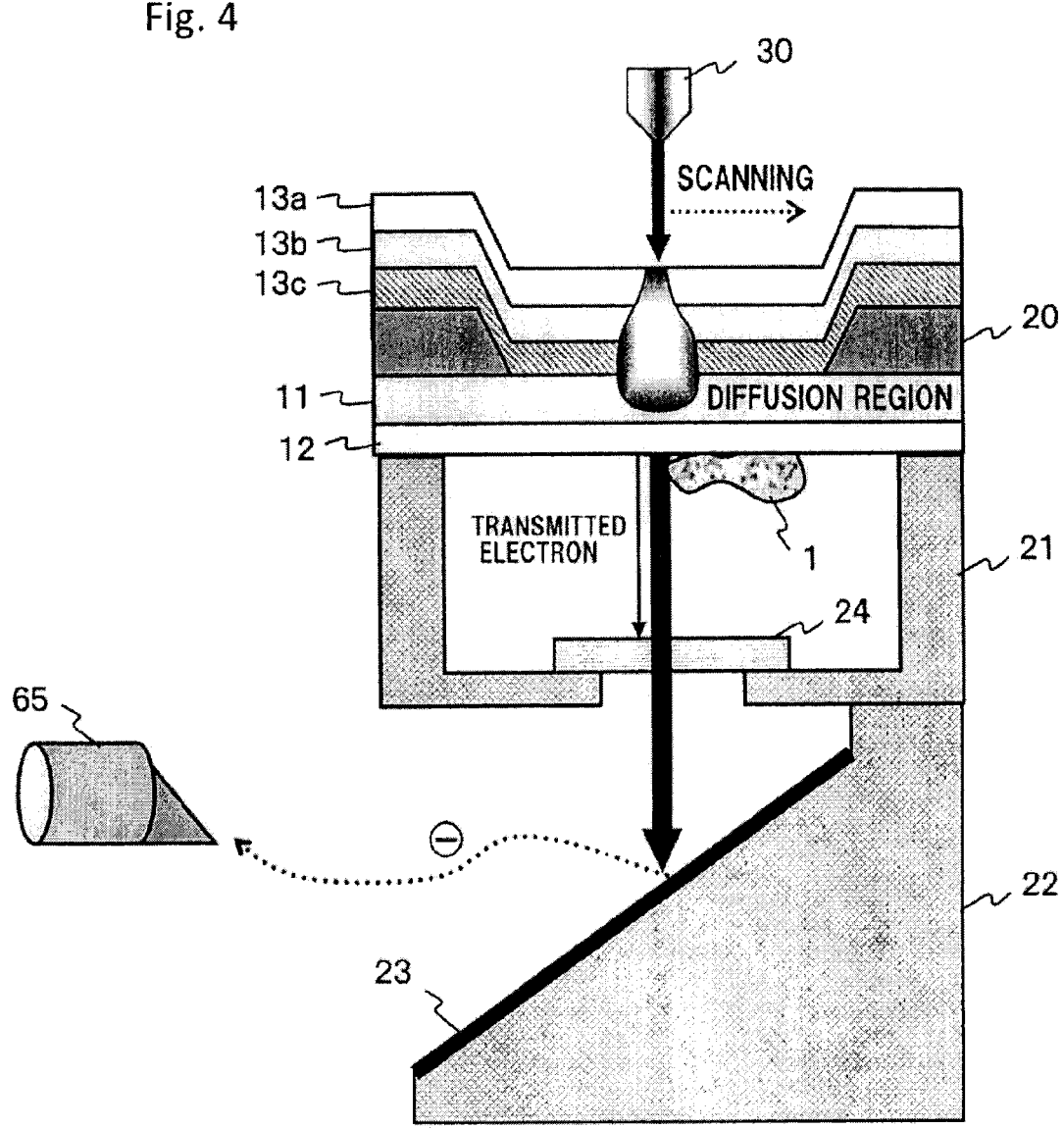
FIG. 4 is a diagram showing an embodiment in which a filter for electron beam shielding is further provided in an X-ray transmission path to the photoelectric conversion surface in the X-ray microscope of the embodiment shown in FIG. 3.

FIG. 4 is a diagram showing an embodiment in which a filter (24) for electron beam shielding is further provided in an X-ray transmission path to the photoelectric conversion surface (23) in the X-ray microscope of the embodiment shown in FIG. 3. The filter (24) shields electron beams while allowing X-rays to pass therethrough. The filter (24) makes it possible to completely restrict the transmitted electrons from being detected by the secondary electron detector (65) to become noise, or the contrast of X-ray microscope image from being reduced.

Further, using a pressure resistant film such as a silicon nitride film as the filter (24) allows the holder supporting portion (21) to function as a specimen containing cell, thereby keeping the interior of the cell to be atmospheric pressure, and further enabling the observation of a solution specimen.

Moreover, the X-ray radiation film (13) of the embodiment shown in FIG. 4 has a multi-layered structure in which a plurality of films (3a to 3c) having different compositions are laminated such that the films are laminated from the irradiation side of electron beam which is a charged particle beam in the order from a carbon film (13a), an aluminum film (13b), and a titanium film (13c), that is, in an order from a film of which principal element has a smaller atomic number to a film of which principal element has a larger atomic number, wherein the energy of each characteristic X-ray is 283 eV, 453 eV, and 1550 eV. Furthermore, while any of these films has a thickness of not more than 100 nm, adopting such a laminated structure allows a plurality of characteristic X-rays to be generated and the characteristic X-rays from all the films to irradiate the observation specimen (1) without being remarkably attenuated.

Figure 5:
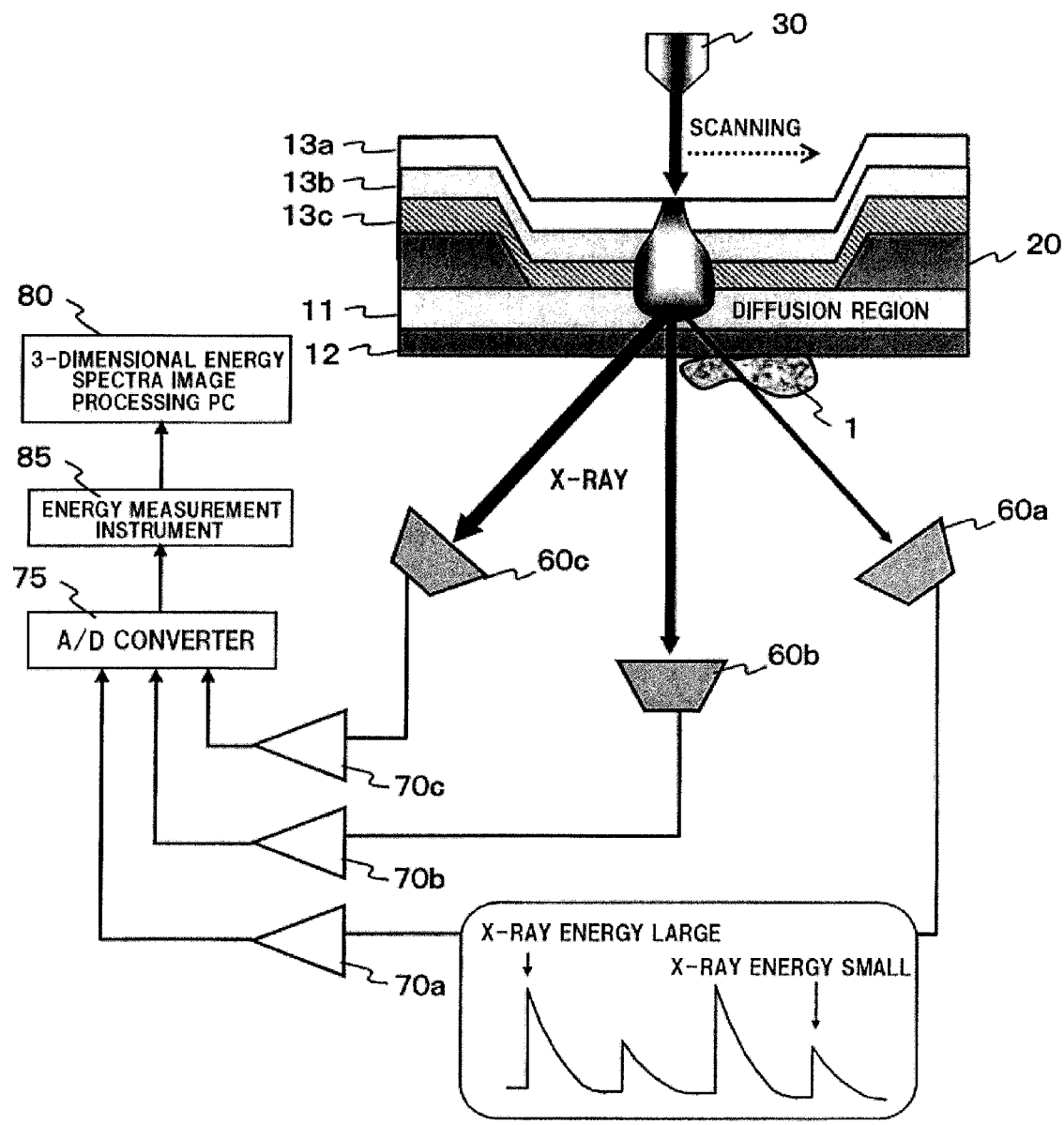
FIG. 5 is a diagram showing a configuration example in which an X-ray radiation film is configured to be a multi-layered structure in which a plurality of films having different compositions are laminated in the X-ray microscope of the embodiment shown in FIG. 2.

FIG. 5 is a diagram showing a configuration example in which the X-ray radiation film is configured to be a multi-layered structure in which a plurality of films (13a to 13c) having different compositions are laminated in the X-ray microscope of the embodiment shown in FIG. 2, and further silicon drift X-ray detectors (60a to 60c) which are capable of measuring X-ray energy are used as the X-ray detectors (60a to 60c) thereby enabling the three-dimensional analysis of element composition. Moreover, in this configuration, an energy measurement instrument is used as the data recorder (85), and an energy-spectra analysis image processing PC is used as the image processing PC (80). Further, in place of the silicon drift detectors, a PIN photodiode detector etc. may be used.

The X-ray radiation film (13) of this configuration is also laminated from the irradiation side of electron beam which is a charged particle beam in the order of a carbon film (13a), an aluminum film (13b), and a titanium film (13c), and the energy of each characteristic X-ray is 283 eV, 453 eV, and 1550 eV.

According to the energy of these characteristic X-rays, the outputs of the silicone drift X-ray detectors (60a to 60c) vary. To be specific, an output peak is high in the characteristic X-ray of aluminum which has high energy, and an output peak is lower in the characteristic X-ray of carbon which has low energy. After these outputs are A/D converted, the kind of characteristic X-ray and the X-ray intensity thereof at a detection position are determined. Since this processing will result in an X-ray absorption spectroscopic image in the scanning region of charged particle, an elemental analysis (compositional analysis) of the observation specimen can be performed based on this image.

Further, since as described above, each of the X-ray detectors (60a to 60c) is disposed at locations where the observation specimen (10) is viewed from different directions, a plurality of X-ray absorption spectroscopic images are obtained depending on the angle to view the specimen so that three-dimensional absorption spectroscopic information and elemental composition information of the observation specimen can be obtained.

In the case where the object to be observed is a biological specimen, the specimen may be present in a solution. Further, a need may arise to investigate the effects of various chemical agents on the shapes and the like of the biological specimen. Accordingly, in the present invention, in order to address such a need, investigation has been made on a specimen containing cell including the above described specimen supporting member (10), that is, a specimen containing cell having a structure in which a solution containing a specimen to be observed is flowed into the cell to make the specimen adsorb to the above described specimen adsorption film, and a specimen containing cell having a structure including a mechanism to control the inflow of the solution into the cell.

Figure 6A:
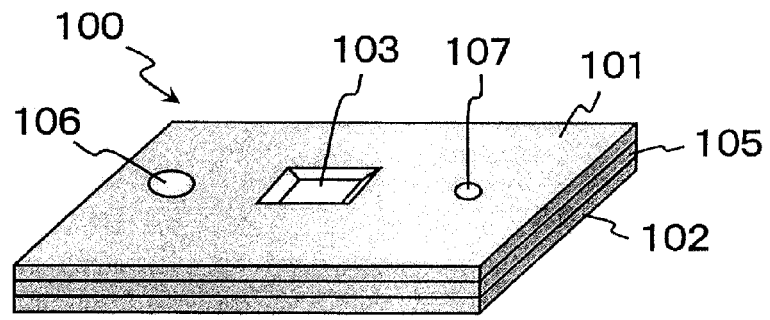
FIG. 6A is a perspective view to explain a configuration example of a specimen containing cell of the present invention.
Figure 6B:
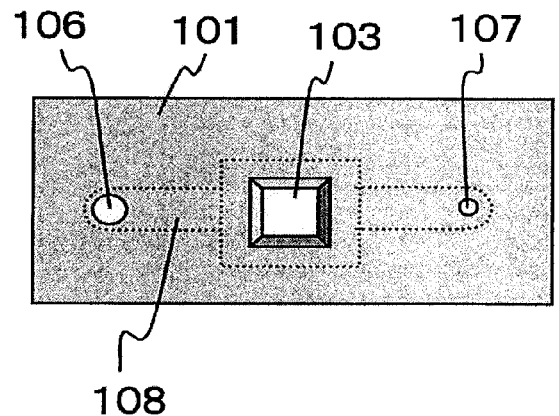
FIG. 6B is a top view to explain a configuration example of the specimen containing cell of the present invention.
Figure 6C:
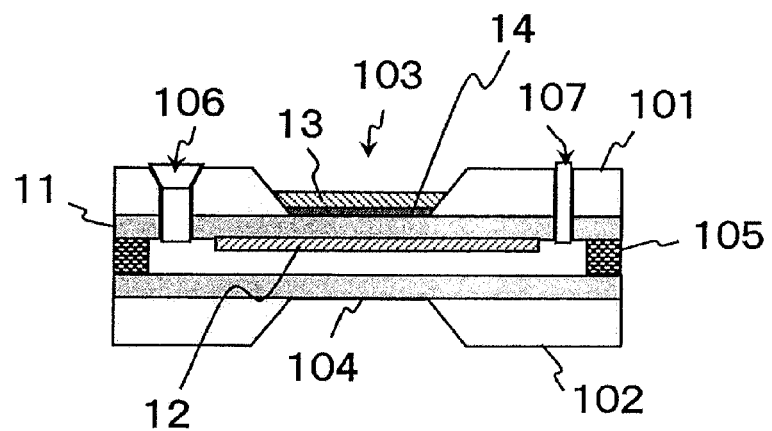
FIG. 6C is a sectional view to explain a configuration example of the specimen containing cell of the present invention.

FIGS. 6A to 6C are diagrams to explain a configuration example of the specimen containing cell of the present invention, wherein FIG. 6A is a perspective view, FIG. 6B is a top view, and FIG. 6C is a sectional view.

The specimen containing cell (100) includes a cell upper portion (101) in which a specimen supporting member (10) for X-ray microscope observation of the present invention is provided, and includes an upper observation window (103) in the central portion thereof, and a cell lower portion (102) which has a lower observation window (104) opposed to the upper observation window (103) on the surface of the cell upper portion (101) on the side of the specimen adsorption film (12), wherein the cell upper portion (101) and the cell lower portion (102) are disposed so as to have a gap of a predetermined width therebetween via a space member (105) which also functions as a seal member.

Moreover, the cell upper portion (101) is provided an injection hole (106) and an air hole (107) for introducing a solution containing an observation specimen into the space formed between the cell upper portion (101) and the cell lower portion (102).

The solution dripped from the injection hole (106) is easily introduced to the observation window (103, 104) along a solution flow path (108) by the action of surface tension since the air hole (107) is provided on the opposite side, and the observation specimen contained in the solution is made to adsorb and be fixed to the specimen adsorption film (12) below the observation window. Further, after the solution is introduced, the injection hole (106) and the air hole (107) are blocked with a sealing member and an air-tight tape, etc. and the specimen containing cell (100) is set in the X-ray microscope.

Figure 7A:
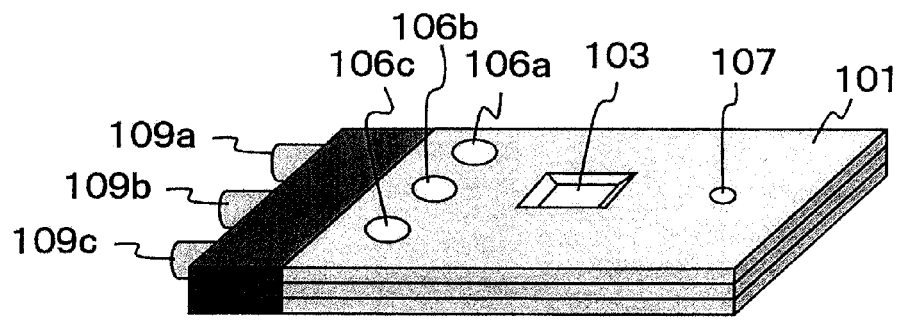
FIG. 7A is a perspective view to explain another configuration example of a specimen containing cell of the present invention.
Figure 7B:
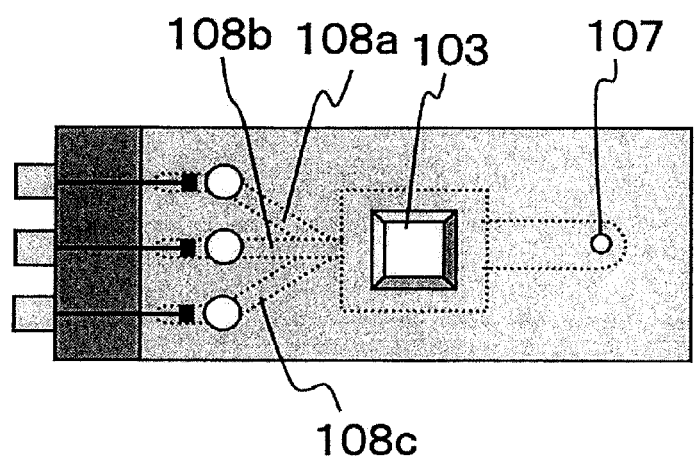
FIG. 7B is a top view to explain a configuration example of the specimen containing cell of the present invention.
Figure 7C:
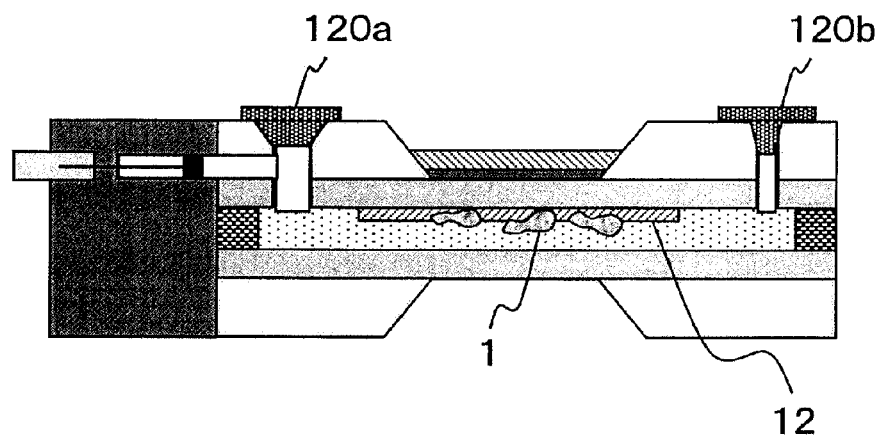
FIG. 7C is a sectional view to explain a configuration example of the specimen containing cell of the present invention.

FIGS. 7A to 7C are diagrams to explain another configuration example of the specimen containing cell of the present invention, wherein FIG. 7A is a perspective view, FIG. 7B is a top view, and FIG. 7C is a sectional view. This specimen containing cell have a plurality of injection holes (106a to 106c), and includes solution flow paths (108a to 108c) associated with each of the plurality of injection holes, in which the solution introduced into a solution flow path is introduced to the observation windows (103, 104) by the action of surface tension.

Further, dampers (109a to 109c) as a pressure application section for pushing out the solution from the injection hole to the specimen adsorption film side are provided in the side portions of the specimen containing cell (100) proximal to each injection holes, and a pressure application valve is provided at a tip end of each of the dampers.

Providing such a plurality of solution flow paths (108a to 108c) will make it easy to perform an experiment in which a reagent etc. is newly fed into a cell which has contained an observation specimen in advance, and the reaction thereby is observed. Further, those components shown by reference characters 120a and 120b are sealing members for blocking the injection hole and the air hole. Such feed-in of solution may be electrophoretically performed without being performed by the pressure application section.

Figure 8A:
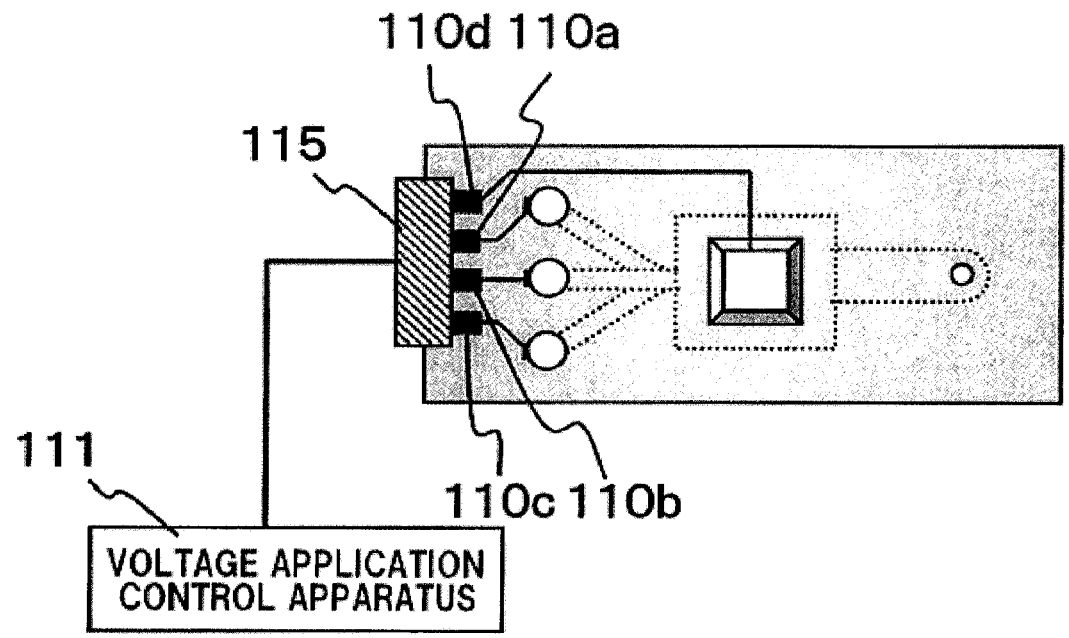
FIG. 8A is a top view to explain a configuration example of a specimen containing cell of the present invention in which the feed-in of solution is performed electrophoretically.
Figure 8B:
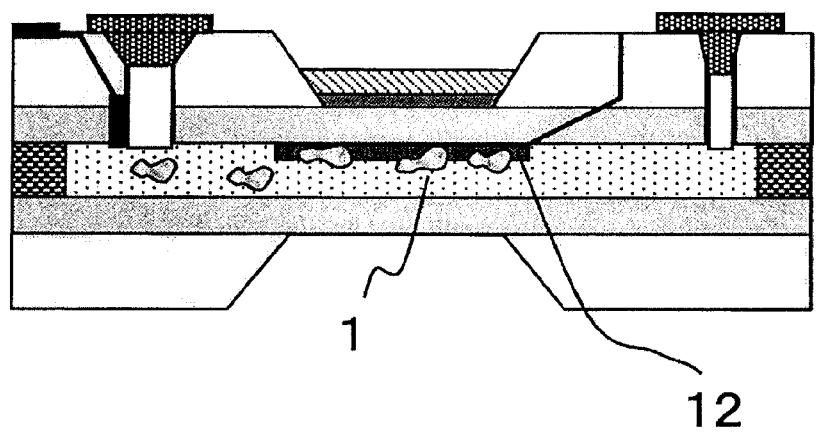
FIG. 8B is a sectional view to explain a configuration example of the specimen containing cell of the present invention in which the feed-in of solution is performed electrophoretically.

FIGS. 8A and 8B are diagrams to explain a configuration example of a specimen containing cell of the present invention, in which the feed-in of solution is performed electrophoretically; FIG. 8A is a top view, and FIG. 8B is a sectional view. Three injection holes (106a to 106c) are provided, and electrodes (110a to 110c) of conductive film are provided in association with respective injection holes. Moreover, being lined up with these electrodes, an electrode (110d) of conductive film for applying voltage to the specimen adsorption film (12) is also provided, and a potential difference is produced by a power supply (111) between the electrode (110a to 110c) of conductive film provided near the injection hole and the specimen adsorption film (12), thereby guiding the observation specimen to the specimen adsorption film side by electrophoresis.

Figure 9A:
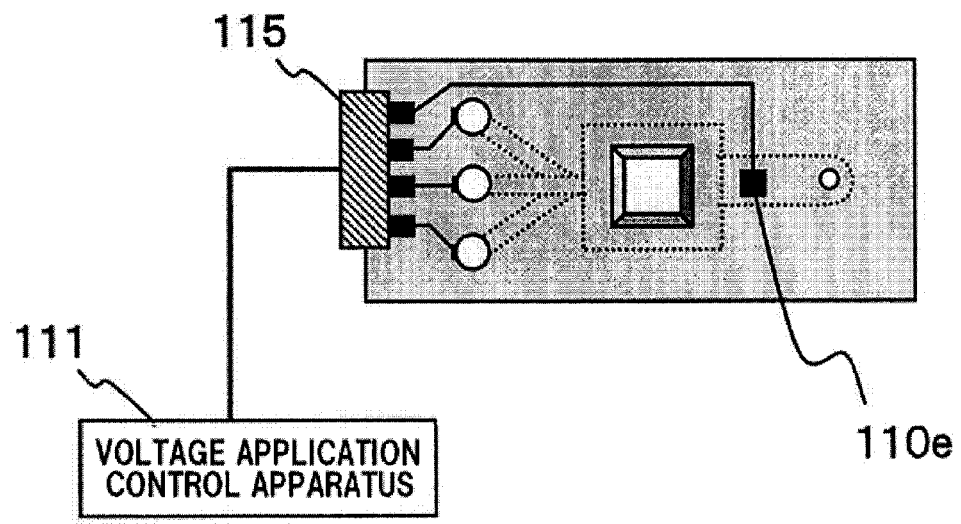
FIG. 9A is a top view to explain another configuration example of a specimen containing cell of the present invention in which the feed-in of solution is performed electrophoretically.
Figure 9B:
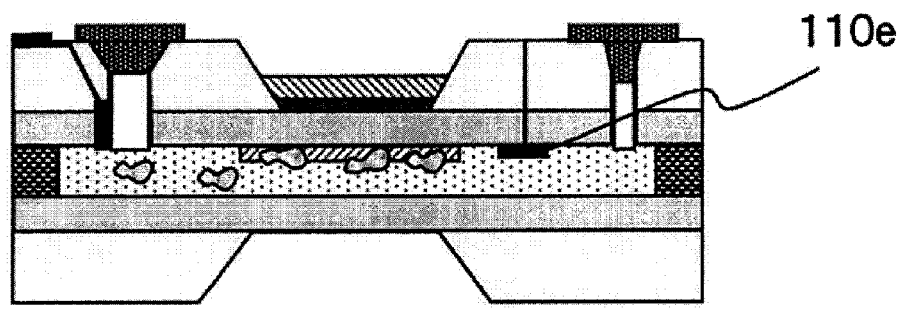
FIG. 9B is a top view to explain another configuration example of the specimen containing cell of the present invention in which the feed-in of solution is performed electrophoretically.

Moreover, when the conductivity of the specimen adsorption film (12) is high, although it is possible to directly connect the specimen adsorption film (12) with the electrode (110d), when the conductivity of the specimen adsorption film (12) is insufficient, a separate electrode (110e) may be provided between the observation window (103) and the air hole (107) as shown in the top view of FIG. 9A and the sectional view of FIG. 9B, thereby promoting electrophoresis of the solution.

In order to obtain a clear image of the specimen to be observed by using the above described specimen containing cell, it is necessary to perform observation under an appropriate condition. In particular, the acceleration voltage and current of charged particle beam, which are observation conditions of the X-ray microscope, are extremely important. For example, the electron beam acceleration voltage when performing X-ray microscope observation by using an SEM needs to be set at a value at which the electron beam will pass through the X-ray radiation film, but will not reach the observation specimen. Such an appropriate condition is determined by the factors such as the material and thickness of each film constituting the specimen supporting member.

Since such conditions cannot be known only by viewing the external appearance of the specimen containing cell, it is desirable, from viewpoint of performing convenient observation, that a cell information recording section for recording information relating to constitutive members is provided in advance in the specimen supporting member itself, or in the specimen containing cell for containing the specimen supporting member, and information on observation conditions and characteristic X-rays to be radiated are preferably, for example, printed thereon. Such cell information recording section may print or engrave characters such as symbols and numerals, a barcode, a QR code, and the like at a position where they can be read from the outside. Moreover, for example, a recording medium such as a semiconductor chip, which is writable and readable from the outside, may be used as the cell information recording section.

Figure 10A:
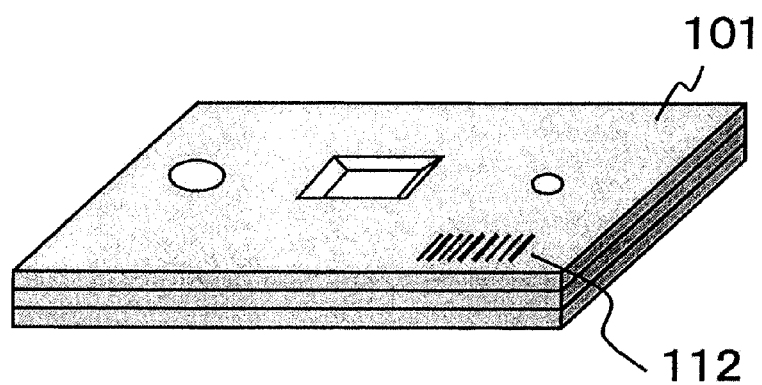
FIG. 10A illustrates an embodiment in which a barcode as a cell information recording section is printed on a cell upper portion of the specimen containing cell shown in FIG. 6A.
Figure 10B:
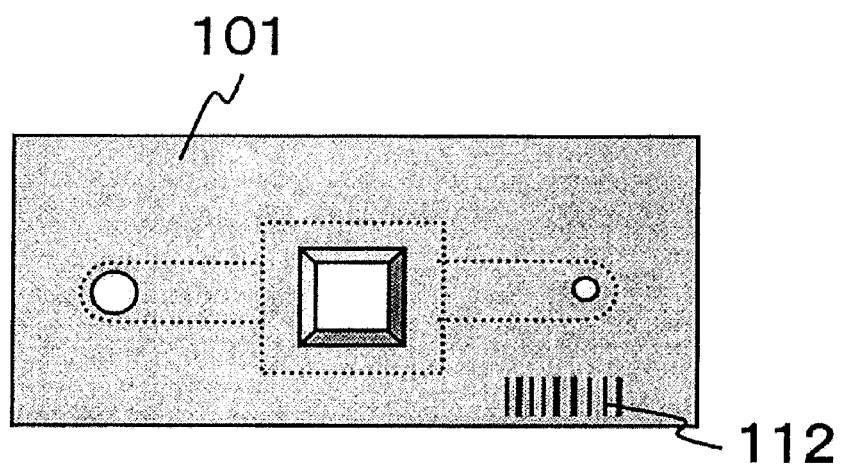
FIG. 10B illustrates an embodiment in which a barcode as a cell information recording section is printed on a cell upper portion of the specimen containing cell shown in FIG. 6B.

FIGS. 10A and 10B illustrate an embodiment in which a barcode (112) as the cell information recording section is printed on the cell upper portion (101) of the specimen containing cell shown in FIGS. 6A and 6B.

Figure 11A:
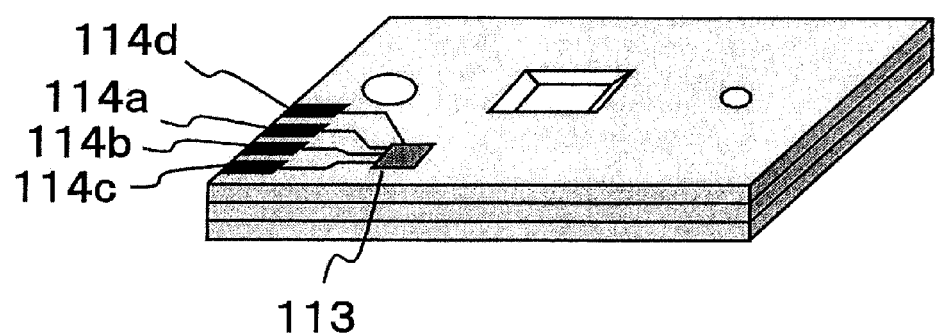
FIG. 11A illustrates an embodiment in which a semiconductor chip as a cell information recording section is provided in a cell upper portion of the specimen containing cell shown in FIG. 6A.
Figure 11B:
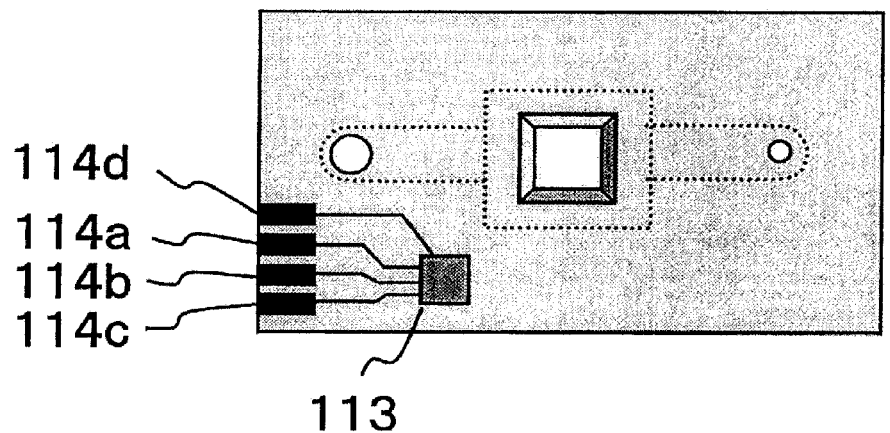
FIG. 11B illustrates an embodiment in which a semiconductor chip as a cell information recording section is provided in a cell upper portion of the specimen containing cell shown in FIG. 6B.

Moreover, FIGS. 11A and 11B illustrate an embodiment in which in place of the above described barcode, a semiconductor chip (113) as the cell information recording section is provided, in which terminal portions (114a to 114d) for enabling the reading and writing to the semiconductor chip (113) is provided in an end portion of the cell upper portion (101). As a matter of course, it is also possible that a device which can read/write information in a non-contact manner is used as the cell information recording section.

Figure 12:
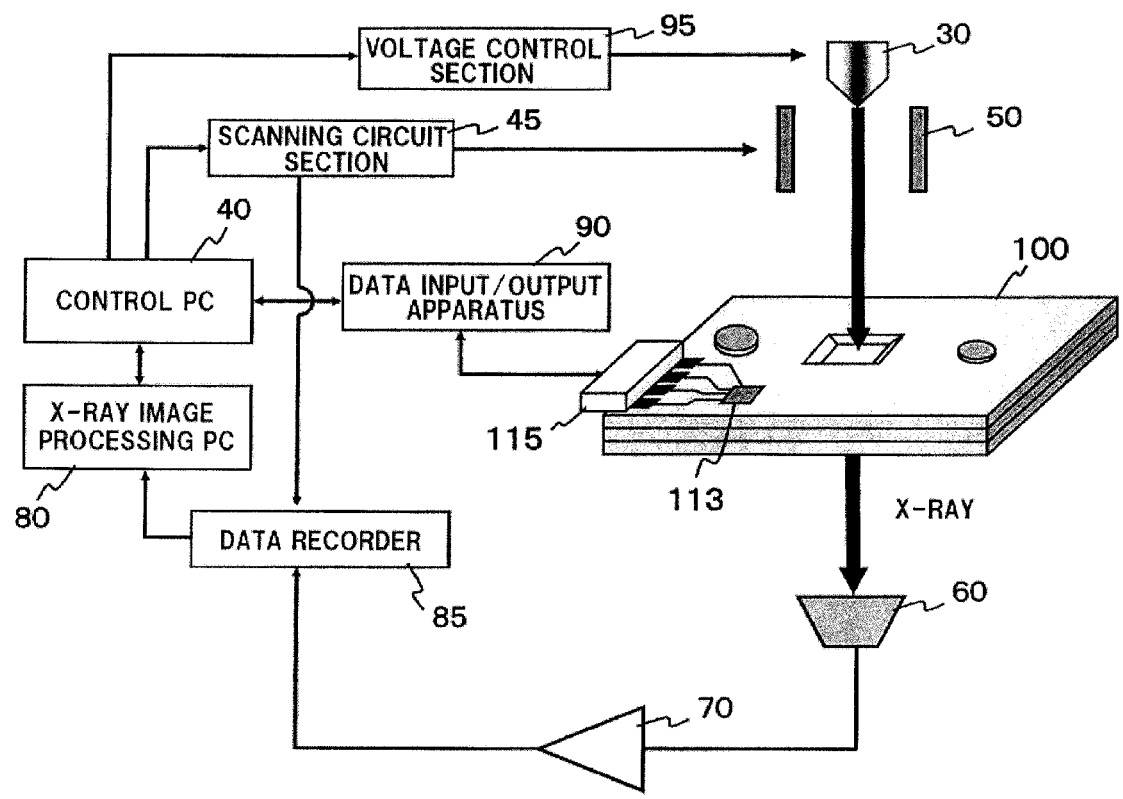
FIG. 12 is a diagram to explain a configuration example of an X-ray microscope when observation is performed by using the specimen containing cell of the embodiment shown in FIGS. 11A and 11B.

FIG. 12 is a diagram to explain a configuration example of an X-ray microscope when observation is performed by using the specimen containing cell of the embodiment shown in FIGS. 11A and 11B. Although the basic apparatus configuration is the same as that shown in FIG. 1, the acceleration voltage of charged particle and appropriate values of current quantity, which are information relating to constitutive members, are read out by the data input/output apparatus (90) from a semiconductor chip (113) provided at an end portion of the cell upper portion (101) of the specimen containing cell (100) via a connector (115). The data input/output apparatus (90) sets an acceleration voltage and current quantity of charged particle based on those information, and the voltage and current quantity to be applied to a voltage control section (95) of the electron gun are controlled by a control PC (40).

An X-ray image obtained by observation is formed by an X-ray image processing PC (80) and fed to the control PC (40), and information on constitutive members etc. of the specimen containing cell is written onto the concerned X-ray image and is saved. Moreover, for the purpose of making it clear when and in what condition the observation specimen was observed, and making use of that for saving and classifying of specimens, configuration may be such that information such as the date and observation conditions of acquiring X-ray images is saved in a semiconductor chip (113), which is the cell information recording section, from the control PC (40) via a connector (115).

Hereafter, the present invention will be described in more detail by way of examples.

Example 1

Figure 13A:
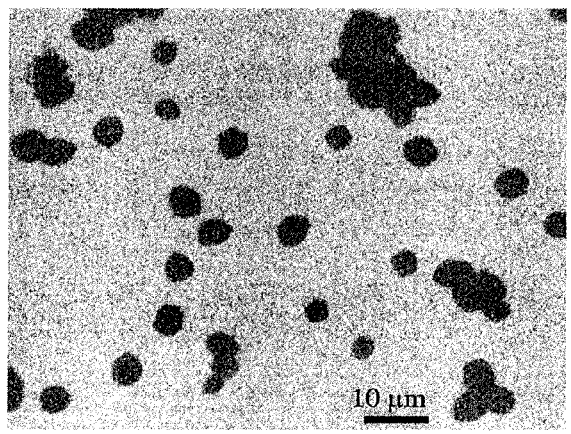
FIG. 13A is an X-ray image obtained by depositing nickel of 120 nm thickness as the specimen adsorption film on a specimen supporting film made up of a silicon nitride film of 50 nm thickness, and fixing and observing yeast with this specimen adsorption film.

FIG. 13A is an X-ray image obtained by vapor depositing a nickel film of 120 nm thickness as the specimen adsorption film on a specimen supporting film made up of a silicon nitride film of 50 nm thickness, and fixing and observing yeast with this specimen adsorption film. Further, FIGS. 13B to 13D are respectively a diagram showing the result of a simulation of the case where an electron beam is made to irradiate the above described specimen supporting member; a diagram showing the result of a simulation of the radiant quantity of characteristic X-ray of nitrogen emitted from the specimen supporting film of silicon nitride at the time of electron beam irradiation shown in FIG. 13B; and a diagram showing the result of a simulation of the X-ray transmittance rate of a nickel film of 120 nm thickness.

Figure 13B:
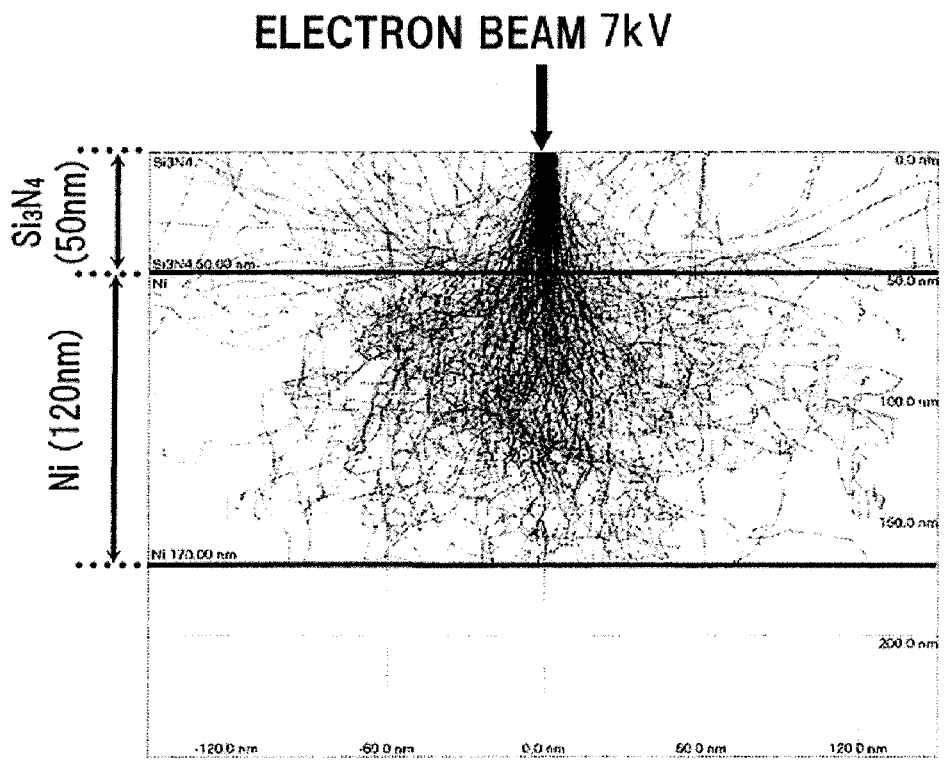
FIG. 13B is a diagram showing the result of a simulation of the case where an electron beam is made to irradiate the above described specimen supporting member.
Figure 13C:
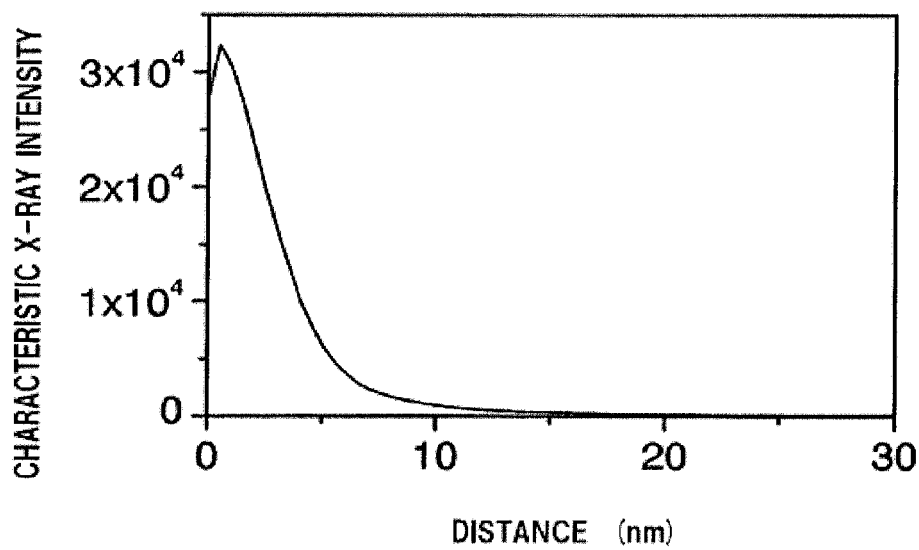
FIG. 13C is a diagram showing the result of a simulation of the radiant quantity of characteristic X-ray of nitrogen emitted from the specimen supporting film of silicon nitride at the time of electron beam irradiation shown in FIG. 13B.

The simulation shown in FIG. 13B shows an electron beam scattering state in the specimen supporting film and the specimen adsorption film obtained by a Monte Carlo simulation, in which the acceleration voltage of electron beam is 7 kV. Since at this level of electron beam acceleration condition, most incident electrons are scattered and absorbed by a nickel film, damages to the observation specimen by the electron beam is almost negligible.

Figure 13D:
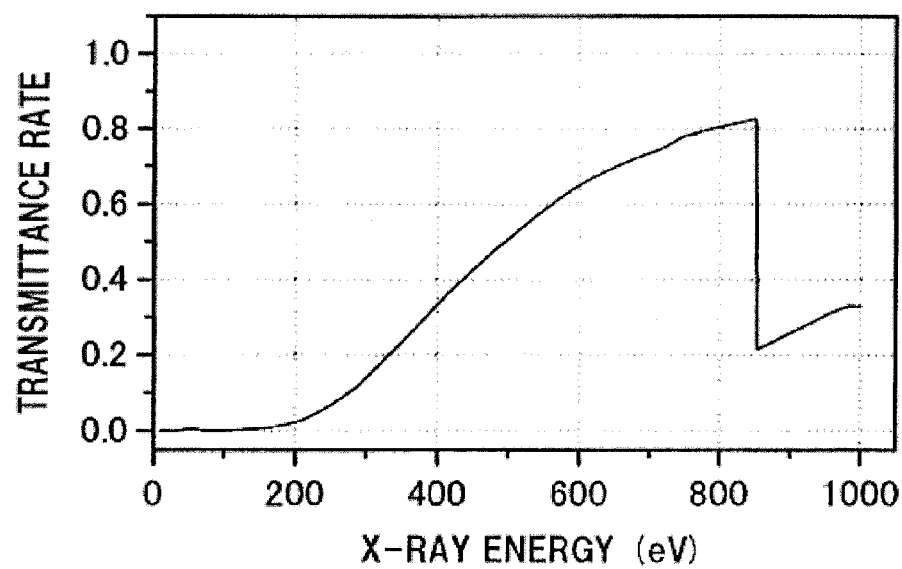
FIG. 13D is a diagram showing the result of a simulation of the X-ray transmittance rate of a nickel film of 120 nm thickness.

While characteristic X-ray of nitrogen (453 eV) is emitted from the silicon nitride film by electron beam irradiation (FIG. 13C), the characteristic X-ray of nitrogen passes through about 40% of a nickel film of 120 nm thickness (FIG. 13D). Therefore, the nickel film, which is the specimen adsorption film, plays a roll of the filter for shielding electron beam and allowing X-ray to pass therethrough at the same time.

Example 2

Figure 14A:
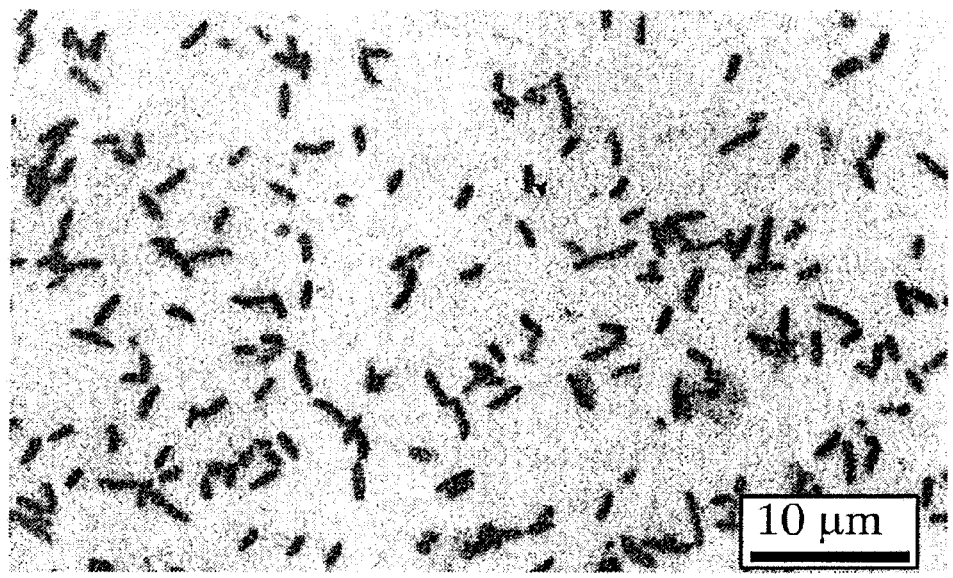
FIG. 14A is an image obtained by vapor depositing a nickel film of 60 nm thickness as a specimen adsorption film on a specimen supporting film made up of a carbon film of 40 nm thickness, and making bacteria as an observation specimen adsorb to the nickel film and observing it at a magnification of 2000.

FIG. 14A is an X-ray image obtained by vapor depositing a nickel film of 60 nm thickness as the specimen adsorption film on the specimen supporting film made up of a carbon film of 40 nm thickness, and making bacteria as an observation specimen absorb to the nickel film and observing it at a magnification of 2000, and it can be confirmed that the bacteria are quite uniformly adsorbed in an appropriate manner.

Figure 14B:
FIG. 14B is an image when the above described observation magnification of the bacteria is raised to 15000.

FIG. 14B is an image when the above described observation magnification of bacteria is raised to 15,000, at which magnification the internal structure of bacterium is observed in detail.

Figure 14C:
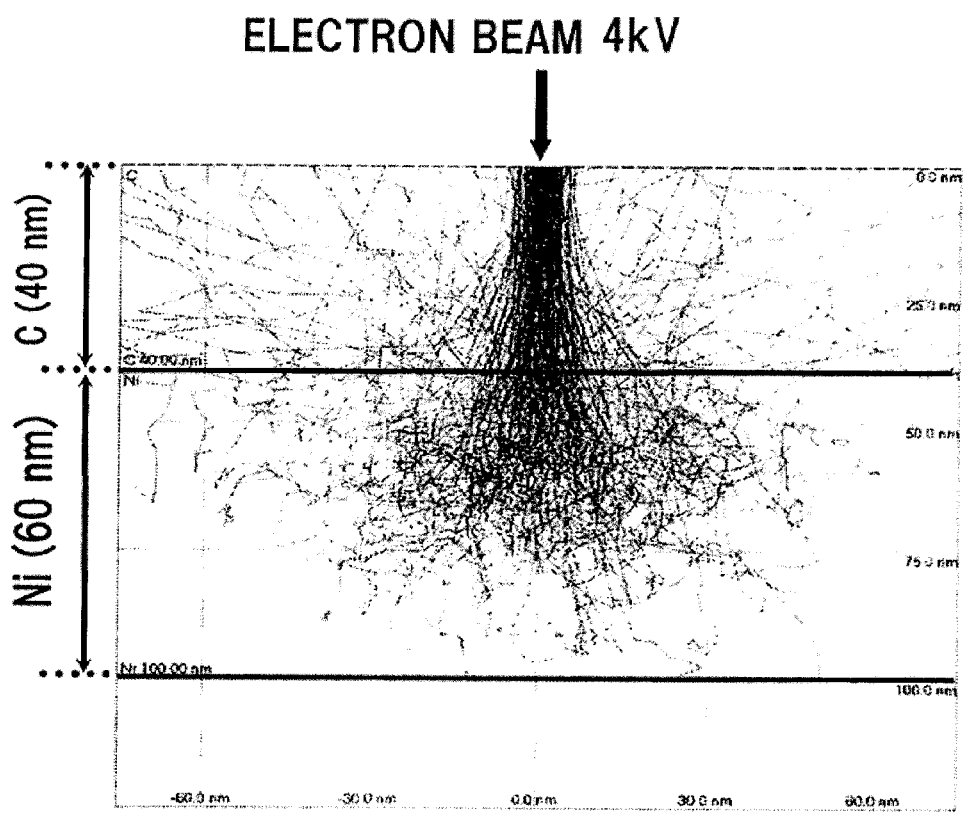
FIG. 14C is a diagram showing the result of a simulation of the case where an electron beam is made to irradiate the above described specimen supporting member.

FIG. 14C is a diagram showing the result of a simulation of the case where an electron beam is made to irradiate the above described specimen supporting member, in which the simulation determined the scattering state of an electron beam in the specimen supporting film and the specimen adsorption film by the Monte Carlo simulation, where the acceleration voltage of electron beam was 4 kv. The irradiation electrons pass through the carbon layer as they are, and are then scattered and absorbed by the nickel film.

Figure 14D:
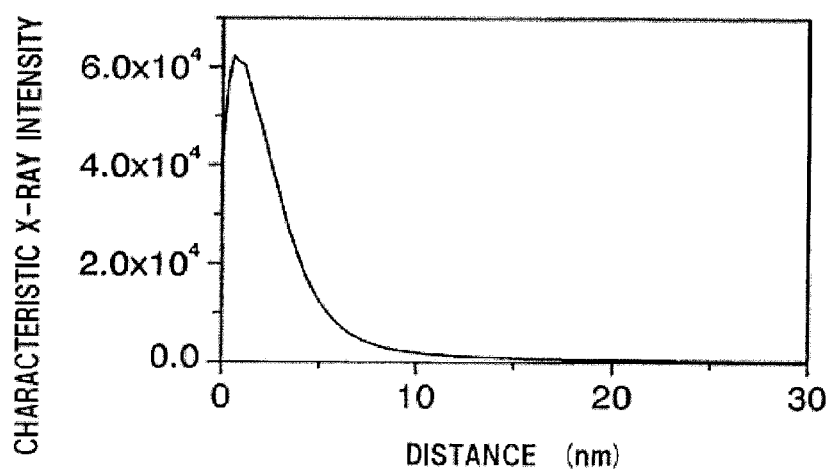
FIG. 14D is a diagram showing the radiation range (the extent of spreading of characteristic X-ray intensity) of a characteristic X-ray generated in a carbon film.

FIG. 14D is a diagram showing the radiation range (the extent of spreading of characteristic X-ray intensity) of a characteristic X-ray generated in a carbon film, wherein although a very strong characteristic X-ray is radiated from the carbon film, since the scattering of electron beam in the carbon film is small, the radiation range is as very small as not more than 5 nm, which enables X-ray observation at a high resolution.

Example 3

Figure 15A:
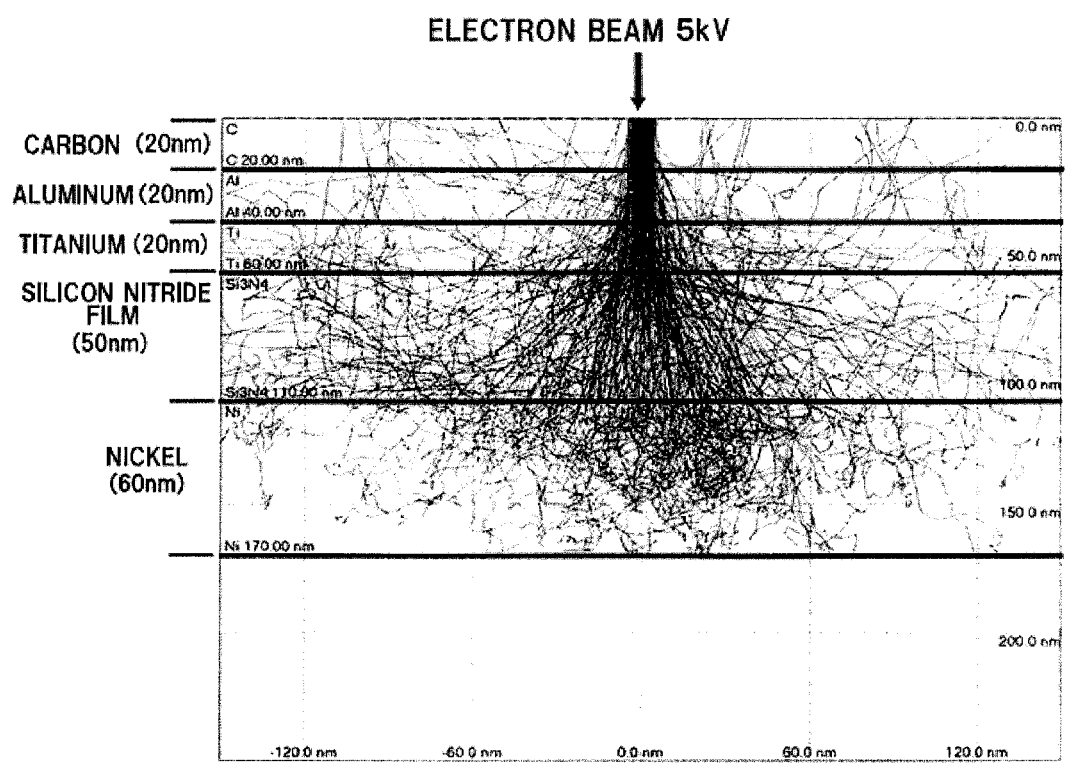
FIG. 15A is diagram showing a scattering state of electron beam determined by a Monte Carlo simulation of an X-ray radiation film in which the lamination is made from the electron bean incidence side in an order from a carbon film (20 nm), an aluminum film (20 nm), and a titanium film (20 nm).

FIG. 15A is a diagram showing a scattering state of electron beam determined by a Monte Carlo simulation when plural kinds of X-ray radiation films are laminated, wherein the lamination is made from the electron beam incidence side in an order from a carbon film (20 nm), an aluminum film (20 nm), and a titanium film (20 nm), and the acceleration voltage of electron beam is 5 kV. Laminating thin films made up of plural kinds of metal allows a plurality of characteristic X-rays to be radiated, enabling the measurement of elementary composition within a specimen from those absorption ratios and the like. Moreover, forming thin film layers by laminating from the electron beam incidence side in an order from a lighter element to a heavier element allows the scattering range of electron beam to be suppressed.

Figure 15B:
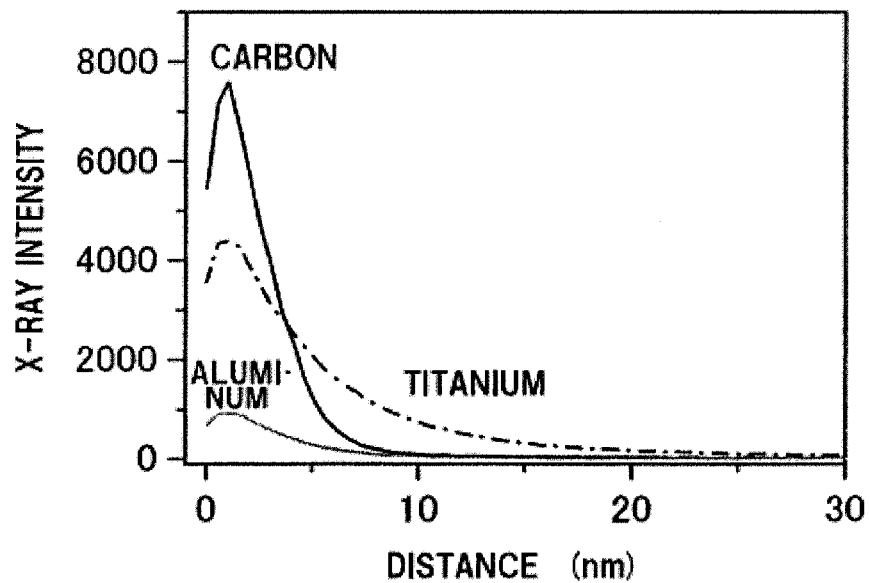
FIG. 15B is a diagram showing the radiation ranges (the extent of spreading of characteristic X-ray intensity) of characteristic X-rays from each of a carbon film (20 nm), an aluminum film (20 nm), and a titanium film (20 nm).

FIG. 15B is a diagram showing the radiation range (the extent of spreading of characteristic X-ray intensity) of characteristic X-rays from each of a carbon film (20 nm), an aluminum film (20 nm), and a titanium film (20 nm), in which it can be confirmed that characteristic X-rays are radiated uniformly from each film.

Figure 15C:
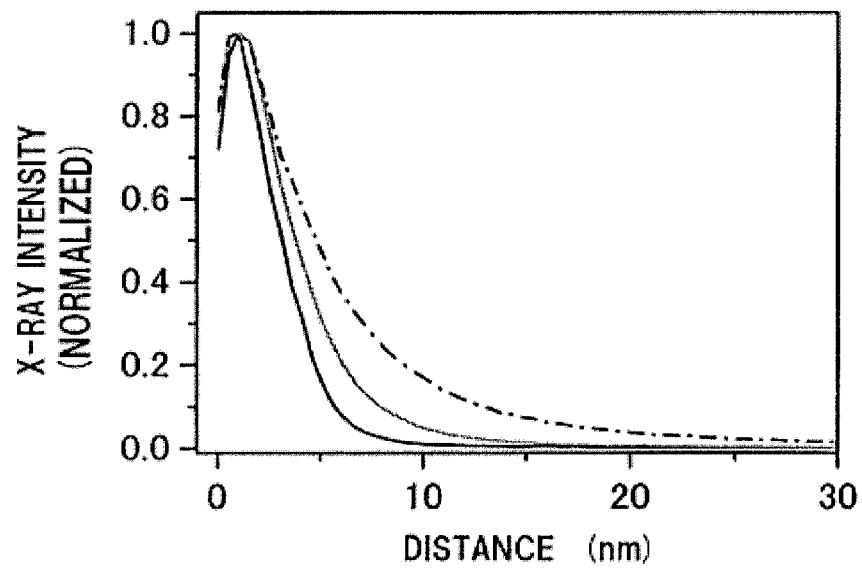
FIG. 15C is a diagram showing the radiation range of the above described characteristic X-rays in a normalized form.

FIG. 15C is a diagram showing the radiation range of the above described characteristic X-rays in a normalized form, from which it is seen that any characteristic X-ray has a half-value width of not more than 5 nm thereby achieving a high resolution.

Figure 16A:
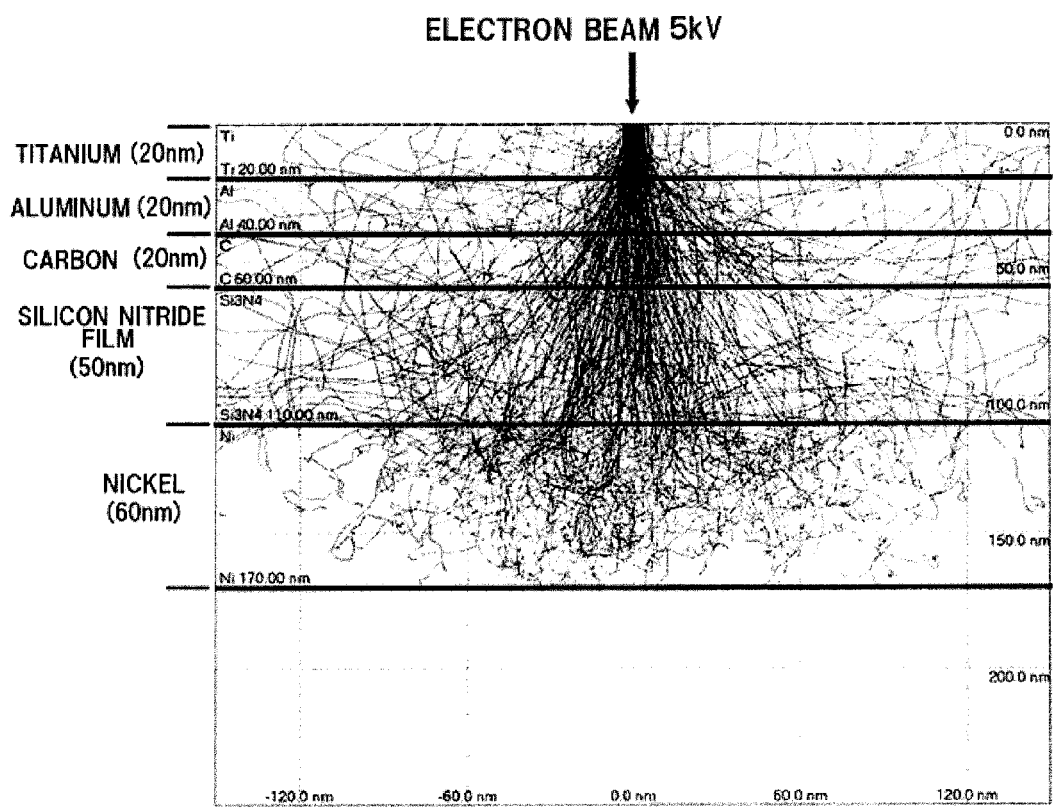
FIG. 16A is diagram showing a scattering state of electron beam determined by a Monte Carlo simulation of an X-ray radiation film in which the lamination is made from the electron bean incidence side in an order from a titanium film (20 nm), an aluminum film (20 nm), and a carbon film (20 nm).

In this regards, determining the scattering state of electron beam of an X-ray radiation film which is laminated from the electron beam incidence side in an order from a titanium film (20 nm), an aluminum film (20 nm), and a carbon film (20 nm) by a Monte Carlo simulation confirms that the scattering range of electron beam will significantly expand (FIG. 16A). This is caused by that the electron beam is significantly scattered by the titanium film into which the electron beam is made incident first.

Figure 16B:
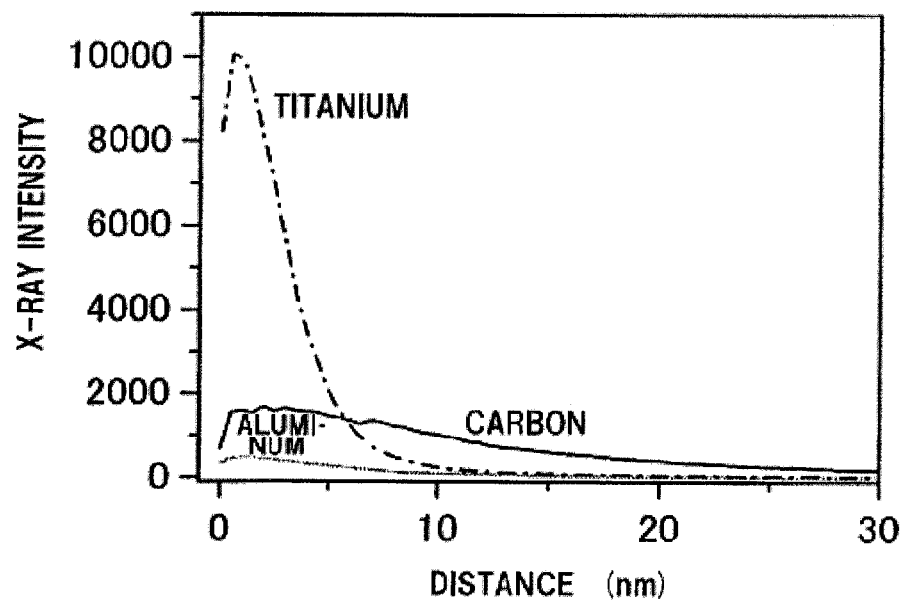
FIG. 16B is a diagram showing the radiation ranges (the extent of spreading of characteristic X-ray intensity) of characteristic X-rays from each of a titanium film (20 nm), an aluminum film (20 nm), and a carbon film (20 nm).
Figure 16C:
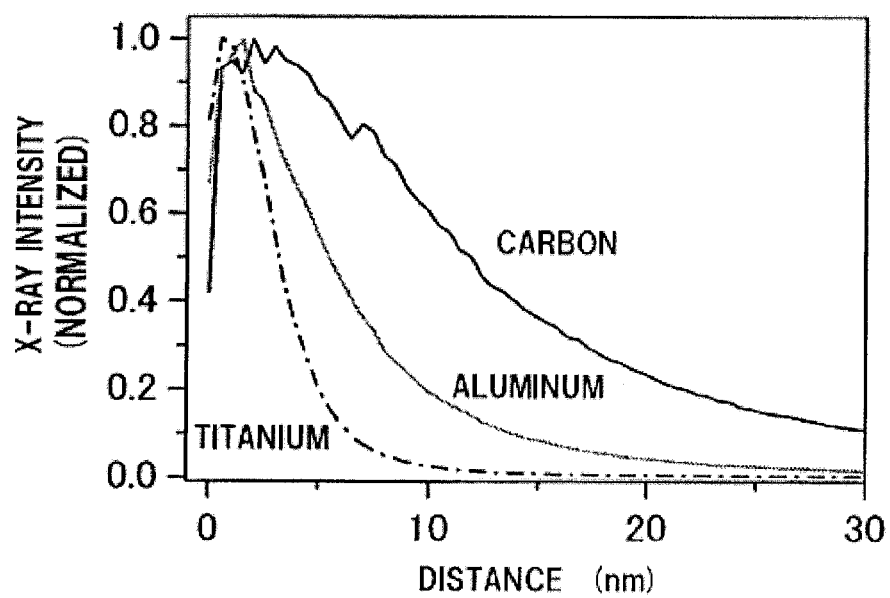
FIG. 16C is a diagram showing the radiation range of the above described characteristic X-rays in a normalized form.

Moreover, titanium exhibits a very large characteristic X-ray intensity and the radiation quantities from carbon and aluminum are reduced (FIG. 16B). Furthermore, an X-ray radiation range obtained by normalizing the result of FIG. 16B confirms that the X-ray radiation ranges of the aluminum film and the carbon film have significantly expanded.

The results described above shows that to suppress the radiation range of characteristic X-ray to be small in an X-ray radiation film in which thin films are laminated, and thereby achieve a high resolution observation, it is necessary to perform the lamination from the charge particle irradiation side in an order from a film of which principal element has a smaller atomic number to a film of which principal element has a larger atomic number.

INDUSTRIAL APPLICABILITY

The present invention provides a specimen supporting member for X-ray microscope image observation suitable for X-ray microscope image observation of a biological specimen, which can shield charged particles passing through to the observation specimen side thereby reducing damages to the specimen, and at the same time, which is less likely to degrade the image quality of the X-ray observation image, and furthermore exhibits little deterioration due to temperature and humidity changes or ultra violet irradiation, etc., and also exhibits excellent durability.

REFERENCE SIGNS LIST

1 Specimen to be observed
10 Specimen supporting member
11 Specimen supporting film
12 Specimen adsorption film
13 X-ray radiation film
14 Charged-particle shielding film
20 Holder
21 Holder supporting portion
22 Photoelectric conversion mechanism section
23 Photoelectric conversion surface
24 Filter for electron beam shielding
30 Electron gun
40 Control PC
45 Scanning circuit section
50 Deflection coil
60 X-ray detector
65 Secondary electron detector
70 Amplifier
75 A/D converter
80 X-ray image processing PC 85 Data recorder
90 Data input/output apparatus
95 Voltage control section
100 Specimen containing cell
101 Cell upper portion
102 Cell lower portion
103 Upper observation window
104 Lower observation window
105 Space member
106 Injection hole
107 Air hole
108 Solution flow path
109a to 109c Damper
110a to 110e Electrode
111 Power supply
112 Barcode
113 Semiconductor chip
114a to 114d Terminal portion
115 Connector
120a, 120b Sealing member

The invention claimed is:

1. A specimen supporting member comprising:
a specimen supporting film;
an X-ray radiation film disposed on one principal surface of the specimen supporting film, wherein the X-ray radiation film radiates a characteristic X-ray in a soft X-ray region upon irradiation with charged particles; and
a specimen adsorption film, which is a metal film disposed on another principal surface of the specimen supporting film, and which fixes by adsorption a specimen to be observed.

2. The specimen supporting member of claim 1, wherein the specimen adsorption film is a metal film comprising an element selected from the group consisting of nickel, cobalt, copper, zinc, iron, manganese, chromium, gold, and platinum.

3. The specimen supporting member claim 1, wherein a thickness of the specimen supporting member is not more than 300 nm.

4. The specimen supporting member of claim 1, wherein the X-ray radiation film comprises carbon, aluminum, scandium, titanium, vanadium, chromium, nickel, silicon, germanium, or an oxide or nitride thereof.

5. The specimen supporting member of claim 4, wherein the X-ray radiation film comprises a plurality of films having different compositions, wherein the plurality of films are laminated.

6. The specimen supporting member of claim 5, wherein at least one of the plurality of films having different compositions has a thickness of not more than 100 nm.

7. The specimen supporting member of claim 5, wherein the plurality of films having different compositions are laminated from a charged-particle irradiation side in an order from a film whose principal element has a smaller atomic number to a film whose principal element has a larger atomic number.

8. The specimen supporting member of claim 5, wherein the plurality of films having different compositions are laminated from a charged-particle irradiation side in an order from a film made of a material having a lighter composition mass to a film made of a material having a heavier composition mass.

9. The specimen supporting member of claim 1, further comprising
a charged-particle shielding film between the specimen supporting film and the X-ray radiation film, or between the specimen supporting film and the specimen adsorption film.

10. The specimen supporting member of claim 9, wherein the charged-particle shielding film comprises a metal element selected from the group consisting of gold, platinum, palladium, osmium, tungsten, tin, cobalt, and nickel.

11. The specimen supporting member claim 1, wherein the specimen supporting film is a silicon nitride film, a carbon film, or a polyimide film.

12. The specimen supporting member of claim 1, wherein the specimen supporting film has a thickness of not more than 200 nm.

13. A specimen containing cell comprising:
a cell upper portion comprising the specimen supporting member of claim 1; and
a cell lower portion having an observation window opposed to a surface of the cell upper portion on a side of the specimen adsorption film, wherein
the cell upper portion and the cell lower portion are disposed so as to have a gap of a predetermined width therebetween via a space member.

14. The specimen containing cell of claim 13, further comprising
an injection hole formed between the cell upper portion and the cell lower portion, and
an air hole,
wherein the injection hole is suitable for introducing an observation specimen.

15. The specimen containing cell of claim 14, further comprising
a plurality of the injection holes, and
a plurality of flow paths associated with each of the plurality of injection holes.

16. The specimen containing cell of claim 14, further comprising
a conductive film disposed in the vicinity of the injection hole, and
a voltage application section that produces a potential difference between the conductive film and the specimen adsorption film to guide the observation specimen by electrophoresis from the injection hole to the specimen adsorption film side.

17. The specimen containing cell of claim 14, further comprising
a pressure application section that pushes out the observation specimen from the injection hole to the specimen adsorption film side in the vicinity of the injection hole.

18. The specimen containing cell of claim 13, further comprising
a cell information recording section that records information relating to a constitutive member of the specimen containing cell.

19. The specimen containing cell of claim 18, wherein the cell information recording section is printed or engraved at a location where reading from outside of the cell is possible.

20. The specimen containing cell of claim 18, wherein the cell information recording section is a recording medium which is readable and writable from outside of the cell.

21. An X-ray microscope, comprising:
a holder that holds the specimen supporting member of claim 1;

a charged particle gun that makes a charged particle beam converged and incident on the X-ray radiation film;
a scanning mechanism section of the charged particle beam;
an X-ray detector that detects X-rays generated from the specimen supporting member as a result of incidence of the charged particle beam; and
a signal processing section that forms an X-ray image based on the detected signal of the X-rays.

22. An X-ray microscope, comprising:
a holder that holds the specimen supporting member of claim 1;
a charged particle gun that makes a charged particle beam converged and incident on the X-ray radiation film;
a scanning mechanism section of the charged particle beam;
a photoelectric conversion section that photoelectrically converts X-rays generated from the specimen supporting member as a result of incidence of the charged particle beam, into an electron beam;
an electron beam detector that detects the photoelectrically converted electron beam; and
a signal processing section that forms an X-ray image based on the detected signal of the electron beam.

23. An X-ray microscope, comprising:
a holder that holds the specimen containing cell according to claim 18;
a charged particle gun that makes a charged particle beam converged and incident on the X-ray radiation film;
a scanning mechanism section of the charged particle beam;
an X-ray detector that detects X-rays generated from the specimen supporting member as a result of incidence of the charged particle beam;
a signal processing section that forms an X-ray image based on the detected signal of the X-rays;
a reading section of information recorded at the cell information recording section; and
a control section that sets an acceleration voltage and current quantity of charged particles emitted from the charged particle gun based on the information recorded at the cell information recording section.

24. An X-ray microscope, comprising:
a holder that holds the specimen containing cell according to claim 18;
a charged particle gun that makes a charged particle beam converged and incident on the X-ray radiation film;
a scanning mechanism section of the charged particle beam;
a photoelectric conversion section that photoelectrically converts X-rays generated from the specimen supporting member as a result of incidence of the charged particle beam, into an electron beam;
an electron beam detector that detects the photoelectrically converted electron beam;
a signal processing section that forms an X-ray image based on the detected signal of the electron beam;
a reading section of information recorded at the cell information recording section; and
a control section that sets an acceleration voltage and current quantity of charged particles emitted from the charged particle gun based on the information recorded at the cell information recording section.

25. The X-ray microscope of claim 21, further comprising
a plurality of the X-ray detectors disposed at locations where the observation specimen supported by the specimen supporting member is viewed from a different direction.

26. The X-ray microscope of claim 25, wherein
the signal processing section includes an image processing section that forms a three-dimensional X-ray image based on detected X-ray signals from the plurality of the X-ray detectors.

27. The X-ray microscope of claim 21, wherein
the X-ray detector can analyze energy spectra.

28. The X-ray microscope of claim 27, wherein
the X-ray detector is a silicon drift detector or a PIN photodiode detector.

29. The X-ray microscope claim 23, further comprising
a plurality of the X-ray detectors disposed at locations where the observation specimen supported by the specimen supporting member is viewed from a different direction.

30. The X-ray microscope of claim 29, wherein
the signal processing section includes an image processing section that forms a three-dimensional X-ray image based on detected X-ray signals from the plurality of the X-ray detectors.

31. The X-ray microscope of claim 23, wherein the X-ray detector can analyze energy spectra.

32. The X-ray microscope of claim 31, wherein the X-ray detector is a silicon drift detector or a PIN photodiode detector.

* * * * *